US008476386B2

(12) United States Patent
Liu et al.

(10) Patent No.: US 8,476,386 B2
(45) Date of Patent: Jul. 2, 2013

(54) HYPERBRANCHED POLYMERS AND THEIR APPLICATIONS

(75) Inventors: Ye Liu, Singapore (SG); Decheng Wu, Singapore (SG); Chaobin He, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/415,801

(22) Filed: Mar. 8, 2012

(65) Prior Publication Data

US 2012/0259084 A1 Oct. 11, 2012

Related U.S. Application Data

(63) Continuation of application No. PCT/SG2006/000109, filed on Apr. 28, 2006.

(60) Provisional application No. 60/676,451, filed on Apr. 29, 2005.

(51) Int. Cl.
C08F 12/28 (2006.01)
C08F 26/00 (2006.01)
C08F 20/10 (2006.01)
C08G 67/02 (2006.01)
C08G 63/44 (2006.01)
C08G 69/26 (2006.01)

(52) U.S. Cl.
USPC ........... 526/263; 526/310; 526/312; 526/318; 526/318.44; 526/328; 528/392; 528/286; 528/332; 528/335

(58) Field of Classification Search
USPC .................... 526/318.44, 310, 312, 218, 263, 526/328; 528/392, 288, 332, 335
See application file for complete search history.

(56) References Cited

U.S. PATENT DOCUMENTS 5,166,320 A 11/1992 Wu et al.
5,399,346 A 3/1995 Anderson et al.

FOREIGN PATENT DOCUMENTS

| EP | 1489126 A1 | * 12/2004 |
| JP | 03039366 A | 2/1991 |
| WO | WO 93/18759 A1 | 9/1993 |
| WO | WO 93/19768 A1 | 10/1993 |
| WO | WO 94/25608 A1 | 11/1994 |
| WO | WO 95/02397 A1 | 1/1995 |
| WO | WO 95/05452 A2 | 2/1995 |

OTHER PUBLICATIONS

Kim et al. "Synthesis of Biodegradable Cross-Linked Poly(β-amino ester) for Gene Delivery and Its Modification, Inducing Enhanced Transfection Efficiency and Stepwise Degradation", Bioconjugate Chem. 2005, 16, 1140-1148.*

(Continued)

*Primary Examiner* — Michael M Bernshteyn
(74) *Attorney, Agent, or Firm* — Kilpatrick Townsend & Stockton LLP

(57) ABSTRACT

The present invention provides a branched, a dendritic, or a hyperbranched poly(amino ester) having a polymer backbone comprising a plurality of branches, wherein the polymer backbone has at least one secondary and at least one tertiary amine linkage. Branched poly(amino ester)s are prepared via a Michael addition reaction of a tris(acrylate ester)monomer with a diamine monomer. In one aspect, the diamine monomer has a primary amino group and a secondary amino group. The poly(amino ester) compounds can be end-capped by reacting with a suitable agent. The present invention also provides applications including, but are not limited to, the delivery of bioactive agents, such as drugs, DNA or RNA; or biocompatible imaging.

9 Claims, 10 Drawing Sheets

OTHER PUBLICATIONS

Hu et al. "Fast growing dendritic poly(ester-amines) from alternate reaction of EDA and TMPTA", Tetrahedron Letters 46 (2005), 2503-2500.*

Xu et al. "Fast growing dendritic poly(ester-amines) from alternate reaction of EDA and TMPTA", Tetrahedron Letters 46 (2005), 2503-2500.*

Anderson, W. French, "The best of times, the worst of times," *Science*, Apr. 2000, vol. 288, p. 627-629.

Cavazzana-Calvo et al., "Gene therapy of human severe combined immunodeficiency (SCID)-X1 disease," *Science*, Apr. 2000, vol. 288, pp. 669-672.

Clapp, D.W. et al., "Fetal liver hematopoietic stem cells as a target for in utero retroviral gene transfer," *Blood*, Aug. 1991, vol. 78, No. 4, pp. 1132-1139.

Cristiano, R.J. et al., "Hepatic gene therapy: Adenovirus enhancement of receptor-mediated gene delivery and expression in primary hepatocytes," *Proc Natl Acad Sci*, USA, Mar. 1993, vol. 90, pp. 2122-2126.

Curiel et al., "Adenovirus enhancement of transferrin-polysine-mediated gene delivery," *Proc Natl Acad Sci*, USA, Oct. 1991, vol. 88, pp. 8850-8854.

Kim et al., Synthesis of biodegradable cross-linked poly(β-amino ester) for gene delivery and its modification, inducing enhanced transfection efficiency and stepwise degradation, *Bioconjucate Chemistry*, 2005, vol. 16, pp. 1140-1148.

Wilson, J.M. et al., "Hepatocyte-directed gene transfer in vivo leads to transient improvement of hypercholesterolemia in low density lipoprotein receptor-deficient rabbits," *J Biol Chem*, Jan. 1992, vol. 267, No. 2, pp. 963-967.

Wu, G. et al., "Receptor-mediated gene delivery and expression in vivo," *J Biol Chem*, Oct. 1988, vol. 263, No. 29, pp. 14621-14624.

Xu Dongmei et al., "Fast growing dendritic(poly-esteramines) from alternate reaction of EDA and TMPTA," *Tetrahedron Letters*, 2005, vol. 46, pp. 2503-2505.

\* cited by examiner

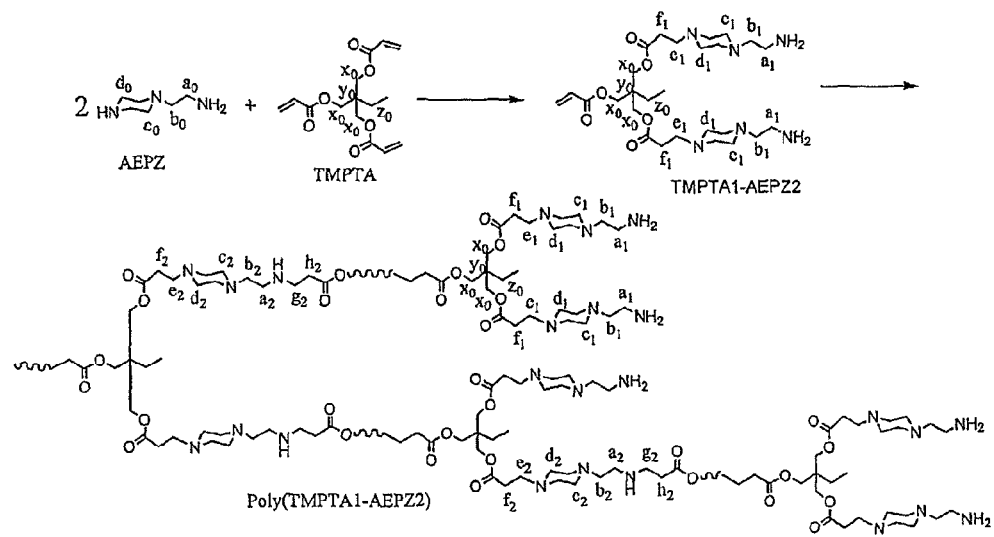
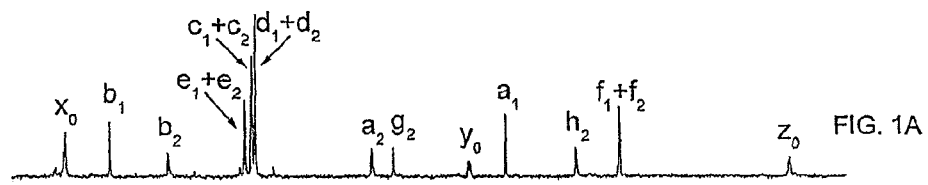
FIG. 1A
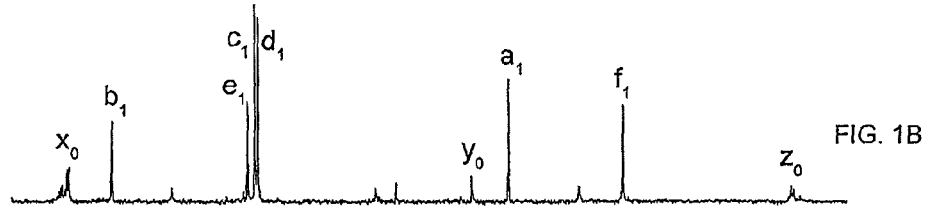
FIG. 1B
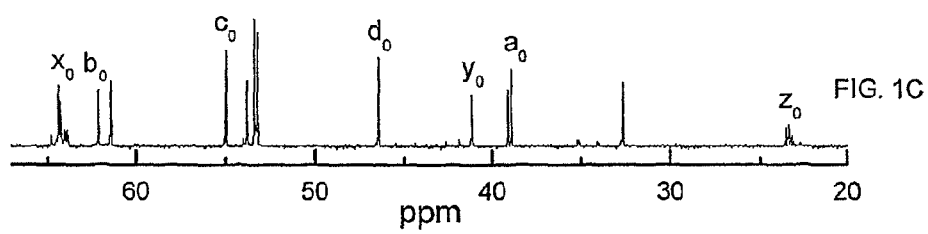
FIG. 1C
FIG. 1

HYPERBRANCHED POLYMERS AND THEIR APPLICATIONS

CROSS-REFERENCES TO RELATED APPLICATIONS

This application is a continuation of PCT/SG2006/000109, filed Apr. 28, 2006, which application claims priority to U.S. Provisional Patent Application No. 60/676,451, filed Apr. 29, 2005, which is hereby incorporated by reference in its entirety for all purposes.

BACKGROUND OF THE INVENTION

There is a need for safe and efficient vectors for delivery of bioactive agents, such as DNA, RNA, protein or drugs because conventional approaches of viral mediated delivery can cause a virus elicted immune response in the patient, or increase the risk of cancer for the patient.

Nonviral vectors have attracted much attention due to their lack of immunogenic problems. Poly(ethyleneimine)s (PEI) have been widely studied as DNA condensing agents and transfecting vectors. However, PEI polymers show significant levels of cytotoxicity both in vitro and in vivo and are not biodegradable, which may not be safe for long-term treatment.

Some poly(ester alkyleneimine)s are potentially useful as vectors for delivery of bioactive agents, in part because the polymers are biodegradable and cationic in physiological solutions and have low cytotoxicity. However, the poly(ester alkyleneimine)s known in the art either have limited solubility in physiological conditions, or are difficult to prepare. Many other types of cationic polymers have been suggested for use as vectors exhibit low transfection efficiency relative to PEI and the transfection efficiency can vary depending on the types of cells being transfected.

Therefore, there is a need to develop other biodegradable polymers to overcome the above and other problems. Surprisingly, the present invention meets this and other needs.

BRIEF SUMMARY OF THE INVENTION

The present invention relates to novel branched, dendritic or hyperbranched poly(amino ester) compounds, having ester linkages or ester-like linkages between two optionally substituted nitrogen units in the polymer backbone. In one aspect, the compounds have at least one secondary amine linkage and at least one tertiary amine linkage in the polymer backbone. Advantageously, the branched poly(amino ester)s have a higher density of secondary and tertiary amino groups, low cytotoxicity, high transfection efficiency and high solubility. In addition, the dendritic structure of the polymers also has the advantage of encapsulating bioactive agents for efficient delivery. The globular-like structures of the dentritic polymers also offer unique advantage of having larger number of amine and ester functionalities per volume, which are essential and important for achieving good biodegradability and high cell transfection efficiency.

The present invention provides biodegradable poly(amino ester)s having ester linkages or ester-like linkages inserted between two optionally substituted nitrogen units. In some embodiments, the polymer backbones comprise at least one secondary amine linkage and at least one tertiary amine linkage, and at least one primary amine at the prephery such that the biodegradable poly(amino ester)s have primary, secondary and tertiary amines with amine constitution similar to that of a hyperbranched polyethylenimine.

According to one aspect, the present invention provides a branched poly(amino ester) compound having the formula:

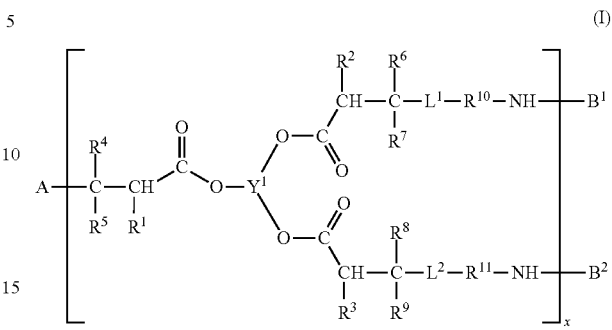

(I)

In formula (I), subscript x is an integer between 1 and about 10,000; each of $R^1$, $R^2$ and $R^3$ is independently selected from the group consisting of hydrogen, deuterium, tritium, hydroxyl, thiohydroxyl and hydrocarbyl; each of $R^4$, $R^5$, $R^6$, $R^7$, $R^8$ and $R^9$ is independently hydrogen, deuterium, tritium, or hydrocarbyl; each of $L^1$ and $L^2$ is independently selected from the group consisting of $NR^{12}$ and $N(-R^{13}-)(-R^{14}-)Z$, wherein each $R^{12}$ is independently hydrocarbyl, hydroxyl or thiohydroxyl and each of $R^{13}$ and $R^{14}$ is bonded to N and Z to form a cyclic structure, and wherein each of $R^{10}$, $R^{11}$, $R^{13}$ and $R^{14}$ is independently oxo, —S—, optionally substituted $C_{1-30}$ alkylene, optionally substituted. $C_{2-30}$ alkenylene, optionally substituted $C_{2-30}$ alkynylene, optionally substituted $C_{3-8}$ cycloalkylene or optionally substituted $C_{6-18}$ arylene, any of which may optionally contain one or more heteroatoms selected from the group consisting of N, O and S; and each Z is independently selected from the group consisting of N, CH, C-hydrocarbyl, trialkyl, triarylene, heteroarylene, tricycloalkylene, triheterocycloalkylene, tris-N,N-dialkylamino, tris-N,N-diarylamino, silyl, a metal and $C(R^aR^b)$, wherein each $R^a$ and $R^b$ is independently a bond, H or hydrocarbyl or together with C join to form a four- to twelve-member carbocyclic or heterocyclic ring, with the proviso that $R^1$, $R^2$, $R^3$, $R^4$, $R^5$, $R^6$, $R^7$, $R^8$, $R^9$ and $R^{12}$ cannot have a primary amino group, a secondary amino group, or a carbon-carbon double bond conjugated to a carbonyl group; $Y^1$ is selected from the group consisting of N, CH, C-hydrocarbyl, trialkyl, triarylene, heteroarylene, tricycloalkylene, triheterocycloalkylene, tris-N,N-dialkylamino, tris-N,N-diarylamino, silyl and a metal; A is selected from the group consisting of H, NH2, hydrocarbyl, silyl, thio, alkylthio, arylthio, hydroxyl, aryloxy, alkylamino, arylamino, heteroaryl, dialkylamino and diarylamino; and each of $B^1$ and $B^2$ is independently H or hydrocarbyl.

In another aspect, the present invention provides a branched poly(amino ester) compound having the formula:

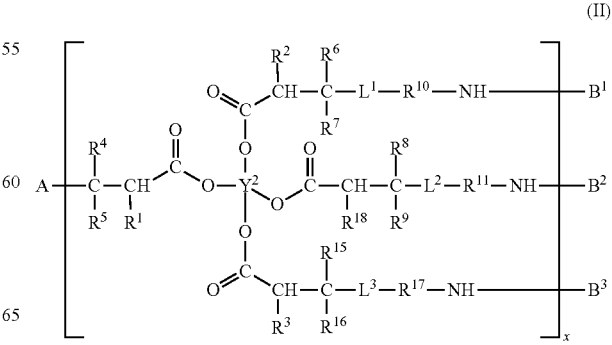

(II)

In the formula (II), subscript x is independently an integer between 1 to about 10,000; each of $R^1$, $R^2$, $R^3$ and $R^{18}$ is independently selected from the group consisting of hydrogen, deuterium, tritium, hydroxyl, thiohydroxyl and hydrocarbyl; each $R^4$, $R^5$, $R^6$, $R^7$, $R^8$, $R^9$, $R^{15}$ and $R^{16}$ is independently hydrogen, deuterium, tritium or hydrocarbyl; each of $L^1$, $L^2$ and $L^3$ is independently selected from the group consisting of $NR^{12}$ and $N(—R^{13}—)(—R^{14}—)Z$, wherein each $R^{12}$ is independently hydrocarbyl, hydroxyl or thiohydroxyl and each of $R^{13}$ and $R^{14}$ is bonded to N and Z to form a cyclic structure, and wherein each of $R^{10}$, $R^{11}$, $R^{13}$, $R^{14}$ and $R^{17}$ is independently oxo, —S—, optionally substituted $C_{1-30}$ alkylene, optionally substituted $C_{2-30}$ alkenylene, optionally substituted $C_{2-30}$ alkynylene, optionally substituted $C_{3-8}$ cycloalkylene or optionally substituted $C_{6-18}$ arylene, any of which may optionally contain one or more heteroatoms selected from the group consisting of N, O and S; and each Z is independently selected from the group consisting of N, CH, C-hydrocarbyl, trialkyl, triarylene, heteroarylene, tricycloalkylene, triheterocycloalkylene, tris-N,N-dialkylamino, tris-N,N-diarylamino, silyl, a metal and $C(R^aR^b)$, wherein each $R^a$ and $R^b$ is independently a bond, H or hydrocarbyl or together with C join to form a four- to twelve-member carbocyclic or heterocyclic ring, with the proviso that $R^1$, $R^2$, $R^3$, $R^4$, $R^5$, $R^6$, $R^7$, $R^8$, $R^9$, $R^{12}$, $R^{15}$, $R^{16}$ an $R^{18}$ cannot have a primary amino group, a secondary amino group, or a carbon-carbon double bond conjugated to a carbonyl group; $Y^2$ is selected from the group consisting of C, silyl, tetralkyl, tetraaryl, tetraarylene, tetra-N,N-dialkylamino, tetra-N,N-diarylamino, tetraheteroalkylene, tetracycloalkylene, heteroarylene, and a metal; A is selected from the group consisting of H, $NH_2$, hydrocarbyl, silyl, thio, alkylthio, arylthio, hydroxyl, aryloxy, alkylamino, arylamino, heteroaryl, dialkylamino and diarylamino; each of $B^1$, $B^2$ and $B^3$ is independently H or hydrocarbyl.

In yet another aspect, a method for preparing a branched poly(amino ester) is provided. The method includes reacting an acrylate monomer having the formula:

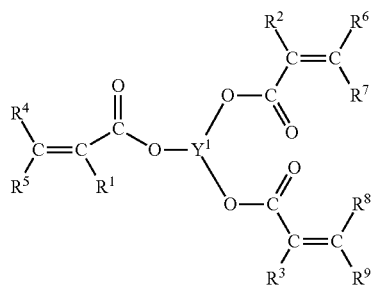

(V)

with a diamine monomer having a formula selected from the group consisting of:

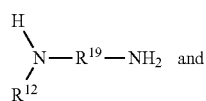

(VI)

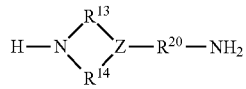

(VII)

In the above formulae, each of $R^1$, $R^2$ and $R^3$ is independently selected from the group consisting of hydrogen, deuterium, tritium, hydroxyl, thiohydroxyl and hydrocarbyl; each of $R^4$, $R^5$, $R^6$, $R^7$, $R^8$ and $R^9$ is independently hydrogen, deuterium, tritium, or hydrocarbyl; $R^{12}$ is hydrocarbyl or hydroxyl or thiohydroxyl; each of $R^{13}$, $R^{14}$, $R^{19}$ and $R^{20}$ is independently oxo, —S—, optionally substituted $C_{1-30}$ alkylene, optionally substituted $C_{2-30}$ alkenylene, optionally substituted $C_{2-30}$ alkynylene, optionally substituted $C_{3-8}$ cycloalkylene or optionally substituted $C_{6-18}$ arylene, any of which may optionally contain one or more heteroatoms selected from the group consisting of N, O and S; $Y^1$ is selected from the group consisting of N, CH, C-hydrocarbyl, trialkyl, triarylene, heteroarylene, tricycloalkylene, triheterocycloalkylene, tris-N,N-dialkylamino, tris-N,N-diarylamino, silyl and a metal; and Z is independently selected from the group consisting of N, CH, C-hydrocarbyl, trialkyl, triarylene, tris-N,N-dialkylamino, tris-N,N-diarylamino, silyl, a metal and $C(R^aR^b)$, wherein each of $R^a$ and $R^b$ is independently a bond, H or hydrocarbyl or together with C join to form a four- to twelve-member carbocyclic or hetercyclic ring, with the proviso that $R^1$, $R^2$, $R^3$, $R^4$, $R^5$, $R^6$, $R^7$, $R^8$, $R^9$ and $R^{12}$ cannot have a primary amino group, a secondary amino group, or a carbon-carbon double bond conjugated to a carbonyl group.

In still another aspect, a method for preparing a branched poly(amino ester) is provided. The method includes homopolymerizing a monomer having the formula:

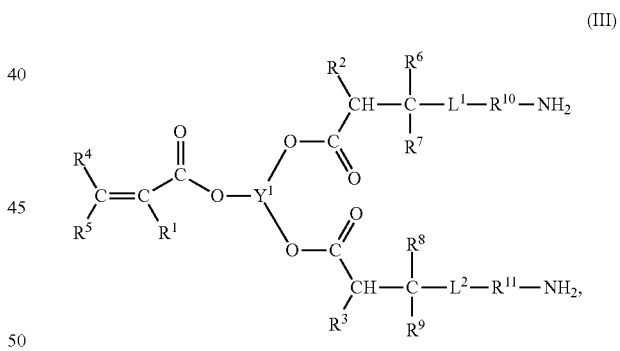

(III)

In the above formula, each of $R^1$, $R^2$ and $R^3$ is independently selected from the group consisting of hydrogen, deuterium, tritium, hydroxyl, thiohydroxyl and hydrocarbyl; each of $R^4$, $R^5$, $R^6$, $R^7$, $R^8$ and $R^9$ is independently hydrogen, deuterium, tritium, or hydrocarbyl; each of $L^1$ and $L^2$ is independently selected from the group consisting of $NR^{12}$ and $N(—R^{13}—)(—R^{14}—)Z$, wherein each of $R^{13}$ and $R^{14}$ is bonded to N and Z to form a cyclic structure, and wherein each $R^5$ is independently hydrocarbyl or hydroxyl or thiohydroxyl; each of $R^{13}$, $R^{14}$, $R^{10}$ and $R^{11}$ is independently oxo, —S—, optionally substituted $C_{1-30}$ alkylene, optionally substituted $C_{2-30}$ alkenylene, optionally substituted $C_{2-30}$ alkynylene, optionally substituted $C_{3-8}$ cycloalkylene or optionally substituted $C_{6-18}$ arylene, any of which may optionally contain one or more heteroatoms selected from the group consisting of N, O and S; and each Z is independently selected from the group consisting of N, CH, C-hydrocarbyl, trialkyl, triarylene, heteroarylene, tricycloalkylene, triheterocycloalkylene, tris-N,N-dialkylamino, tris-N,N-diarylamino, silyl, a metal and C($R^a R^b$), wherein each $R^a$ and $R^b$ is independently a bond, H or hydrocarbyl or together with C join to form a four- to twelve-member carbocyclic or hetercyclic ring, with the proviso that $R^1$, $R^2$, $R^3$, $R^4$, $R^5$, $R^6$, $R^7$, $R^8$ and $R^9$ cannot have a primary amino group, a secondary amino group, or a carbon-carbon double bond conjugated to a carbonyl group; and $Y^1$ is a selected from the group consisting of N, CH, C-hydrocarbyl, trialkyl, triarylene, heteroarylene, tricycloalkylene, triheterocycloalkylene, tris-N,N-dialkylamino, tris-N,N-diarylamino, silyl and a metal.

In another further aspect, a method for preparing a branched poly(amino ester) is provided. The method includes homopolymerizing a monomer having the formula:

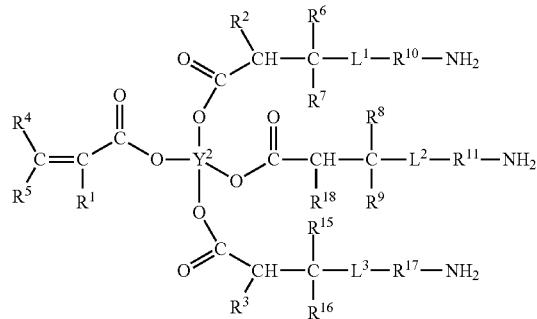

(IV)

In formula (IV), each of $R^1$, $R^2$, $R^3$ and $R^{18}$ is independently selected from the group consisting of hydrogen, deuterium, tritium, hydroxyl, thiohydroxyl and hydrocarbyl; each $R^4$, $R^5$, $R^6$, $R^7$, $R^8$, $R^9$, $R^{15}$ and $R^{16}$ is independently hydrogen, deuterium, tritium or hydrocarbyl; each of $L^1$, $L^2$ and $L^3$ is independently selected from the group consisting of $NR^{12}$ and N(—$R^{13}$—)(—$R^{14}$—)Z, wherein each $R^{12}$ is independently hydrocarbyl, hydroxyl or thiohydroxyl and each of $R^{13}$ and $R^{14}$ is bonded to N and Z to form a cyclic structure, and wherein each of $R^{10}$, $R^{11}$, $R^{13}$, $R^{14}$ and $R^{17}$ is independently oxo, —S—, optionally substituted $C_{1-30}$ alkylene, optionally substituted $C_{2-30}$ alkenylene, optionally substituted $C_{2-30}$ alkynylene, optionally substituted $C_{3-8}$ cycloalkylene or optionally substituted $C_{6-18}$ arylene, any of which may optionally contain one or more heteroatoms selected from the group consisting of N, O and S; and each Z is independently selected from the group consisting of N, CH, C-hydrocarbyl, trialkyl, triarylene, heteroarylene, tricycloalkylene, triheterocycloalkylene, tris-N,N-dialkylamino, tris-N,N-diarylamino, silyl, a metal and C($R^a R^b$), wherein each $R^a$ and $R^b$ is independently a bond, H or hydrocarbyl or together with C join to form a four- to twelve-member carbocyclic or hetercyclic ring, with the proviso that $R^1$, $R^2$, $R^3$, $R^4$, $R^5$, $R^6$, $R^7$, $R^8$, $R^9$, $R^{12}$, $R^{15}$, $R^{16}$ and $R^{18}$ cannot have a primary amino group, a secondary amino group, or a carbon-carbon double bond conjugated to a carbonyl group; $Y^2$ is selected from the group consisting of C, silyl, tetralkyl, tetraaryl, tetraarylene, tetra-N,N-dialkylamino, tetra-N,N-diarylamino, tetraheteroalkylene, tetracycloalkylene, heteroarylene, and a metal; A is selected from the group consisting of H, NH2, hydrocarbyl, silyl, thio, alkylthio, arylthio, hydroxyl, aryloxy, alkylamino, arylamino, heteroaryl, dialkylamino and diarylamino; each of $B^1$, $B^2$ and $B^3$ is independently H or hydrocarbyl.

In still yet another aspect, a method for preparing a branched poly(amino ester) is provided. The method includes reacting an acrylate monomer having the formula:

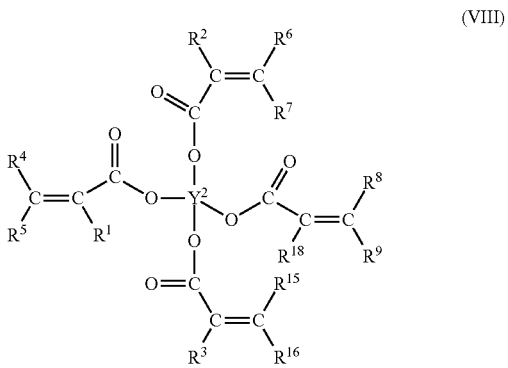

(VIII)

with a diamine monomer having the formula selected from the group consisting of:

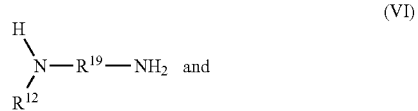

(VI)

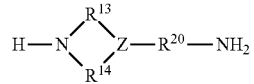

(VII)

In the above formulae, each of $R^1$, $R^2$, $R^3$ and $R^{18}$ is independently selected from the group consisting of hydrogen, deuterium, tritium, hydroxyl, thiohydroxyl and hydrocarbyl; each of $R^4$, $R^5$, $R^6$, $R^7$, $R^8$, $R^9$, $R^{15}$ and $R^{16}$ is independently hydrogen, deuterium, tritium, or hydrocarbyl; $R^{12}$ is independently hydrocarbyl or hydroxyl or thiohydroxyl; each of $R^{13}$, $R^{14}$, $R^{19}$ and $R^{20}$ is independently oxo, —S—, optionally substituted $C_{1-30}$ alkylene, optionally substituted $C_{2-30}$ alkenylene, optionally substituted $C_{2-30}$ alkynylene, optionally substituted $C_{3-8}$ cycloalkylene or optionally substituted $C_{6-18}$ arylene, any of which may optionally contain one or more heteroatoms selected from the group consisting of N, O and S; $Y^2$ is selected from the group consisting of C, silyl, tetralkyl, tetraarylene, tetrakis-N,N-dialkylamino, tetrakis-N,N-diarylamino and a metal; and Z is selected from the group consisting of N, CH, C-hydrocarbyl, trialkyl, triarylene, heteroarylene, tricycloalkylene, triheterocycloalkylene, tris-N, N-dialkylamino, tris-N,N-diarylamino, silyl, a metal and C($R^a R^b$), wherein each $R^a$ and $R^b$ is independently a bond, H or hydrocarbyl or together with C join to form a four- to twelve-member carbocyclic or hetercyclic ring, with the proviso that $R^1$, $R^2$, $R^3$, $R^4$, $R^5$, $R^6$, $R^7$, $R^8$, $R^9$, $R^{12}$, $R^{15}$, $R^{16}$ and $R^{18}$ cannot have a primary amino group, a secondary amino group, or a carbon-carbon double bond conjugated to a carbonyl group.

In a different aspect, the present invention provides a pharmaceutical composition having a branched poly(amino ester) and a bioactive agent.

In a further aspect, a method for preparing a pharmaceutical composition is provided. The method includes solubilizing a branched poly(amino ester) compound of the present invention in an aqueous buffer to obtain a protonated form of the compound, and admixing the protonated form of the compound with a bioactive agent to produce an admixture.

In another aspect, the present invention provides a composition for transfecting a cell having a DNA or a RNA molecule or a salt thereof and a branched poly(amino ester). In some embodiments, a DNA or a RNA molecule or a salt thereof forms a complex with a branched poly(amino ester) compound.

In a further aspect, a method for transfecting a cell is provided. The method includes contacting the cell with a composition having a branched poly(amino ester) complexed with a DNA or a RNA molecule or a salt thereof.

In still yet another aspect, the present invention provides a composition useful as an imaging agent. The composition includes a branched poly(amino ester) and optionally a targeting agent.

In still a further aspect, a use of the composition of the present invention in the preparation of an imaging agent is provided.

BRIEF DESCRIPTION OF THE DRAWINGS

FIG. 1 is a schematic representation of the mechanism of the Michael addition polymerization of a tris(acrylate ester) monomer, such as trimethylpropane triacrylate (TMPTA), with a diamine monomer, such as 1-(2-aminoethyl)piperazine (AEPZ). FIG. 1A-C are $^{13}$C-NMR spectra recorded in situ for the polymerization of TMPTA and AEPZ with a 1:2 feed molar ratio and a monomer concentration of 20% (w/v) at room temperature in $CDCl_3$. Reaction time is 0.40 hr, 11.8 hrs and 197.0 hrs as shown in FIG. 1A, FIG. 1B, and FIG. 1C, respectively.

DETAILED DESCRIPTION OF PRESENT INVENTION

Figure 2:
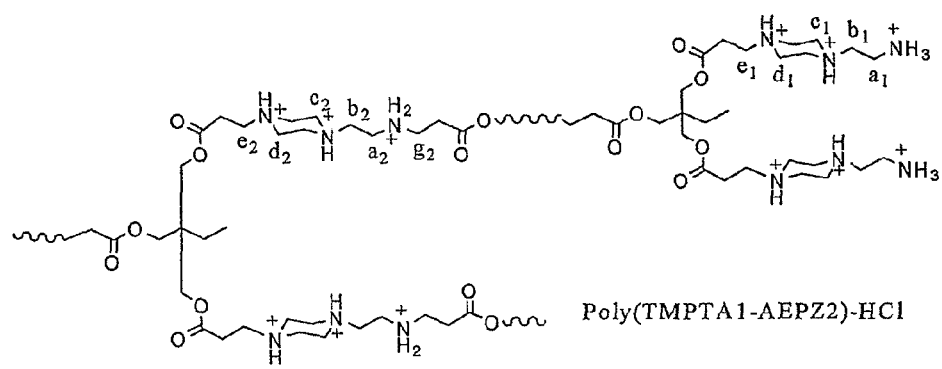
FIG. 2 illustrates a $^{13}$C-NMR spectrum of protonated dendritic poly(amino ester)s formed by reacting TMPTA and AEPZ.
Figure 2:
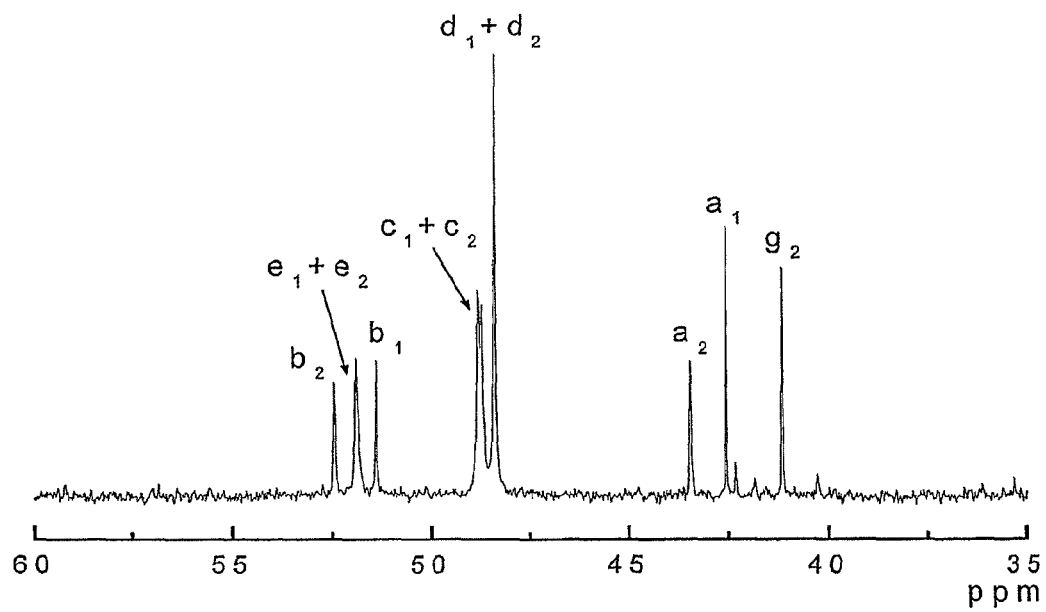

The present invention is related to novel branched, dendritic or hyperbranched poly(amino ester) compounds and their applications. Suitable applications include, but are not limited to, the delivery of bioactive agents, such as drugs, DNA or RNA; or biocompatible imaging.

DEFINITIONS

As used herein, the term "hydrocarbyl" refers to a hydrocarbon radical that may contain one or more heteroatoms and includes, but is not limited to, branched and unbranched alkyl, such as hydroxyalkyl, aminoalkyl, amidylalkyl, thioalkyl, carboxyalkyl, arylalkyl, heteroarylalkyl, silylalkyl, alkylsulfonylalkyl, arylsulfonylalkyl, alkylsulfinylalkyl, arylsulfinylalkyl, alkylsufonylamide, arylsulfonylamide, sulfonlyamidylalkyl, thioalkyl and haloalkyl; branched and unbranched alkenyl, such as hydroxyalkenyl, aminoalkenyl, amidylalkenyl, thioalkenyl, carboxyalkenyl, arylalkenyl, heteroarylalkenyl, silylalkenyl, alkenylsulfonylalkenyl, arylsulfonylalkenyl, alkenylsulfinylalkenyl, arylsulfinylalkenyl, alkenylsufonylamide, arylsulfonylamide, sulfonlyamidylalkenyl and haloalkenyl; branched and unbranched alkynyl, such as hydroxyalkynyl, aminoalkynyl, amidylalkynyl, thioalkynyl, carboxyalkynyl, arylalkynyl, heteroarylalkynyl, silylalkynyl, alkynylsulfonylalkynyl, arylsulfonylalkynyl, alkynylsulfinylalkynyl, arylsulfinylalkynyl, alkynylsufonylamide, arylsulfonylamide, sulfonlyamidylalkynyl and haloalkynyl; aryl, heteroaryl, carbamoyl, carbamoyl-amino, carbamoyl-oxy, thiocarbamoyl, alkoxycarbonyl, aryloxycarbonyl, carbonyldioxy, cyano, alknoyol, aroyl, cycloalkyl, cyclic aromatic, and heterocycloalkyl, each of which may be substituted with one or more substituents selected from the group consisting of branched and unbranched alkyl, branched and unbranched alkenyl, branched and unbranched alkynyl, aryl, heteroaryl, carbamoyl, carbamoyl-amino, carbamoyloxy, thiocarbamoyl, alkoxycarbonyl, aryloxycarbonyl, carbonyldioxy, cyano, alknoyol, aroyl, cycloalkyl, cyclic aromatic, heterocycloalkyl, alkoxy, aryloxy, alkylamino, dialkylamino, arylamino, diarylamino, alkylarylamino, alkylthio, arylthio, carboxyl, amidyl, alkylsilyl, arylsilyl, heteroaryl, sufonyl, sulfinyl, sulfonamide, sulfonate, alkylsulfonyloxy, carbonyldioxy, ureido, thioureido, isocynatyl, hydroxyl, thio, amino and silyl. In the present context, the term "hydrocarbyl" includes hydrocarbon radicals that are linked to the compound via a heteroatom, for example, alkoxy, aryloxy, alkylamino, dialkylamino, arylamino, diarylamino, arylalkylamino, alkylarylamino, alkylthio, arylthio, carboxyl, amidyl, alkylsilyl, arylsilyl, heteroaryl, sufonyl, sulfinyl, sulfonamido, alkylsulfonyloxy, carbonyldioxy, ureido, thioureido and isocynatyl.

As used herein, the term "heteroatom" is meant to include oxygen (O), nitrogen (N), sulfur (S) and silicon (Si).

As used herein, the term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Non-limiting examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

As used herein, the term "heteroalkyl" refers to alkyl groups (or rings) that contain at least one heteroatom selected from N, O, and S, wherein the nitrogen and sulfur atoms are optionally oxidized, and the nitrogen atom(s) are optionally quaternized. A heteroatom can form a double bond with a carbon atom. A heteroalkyl group can be attached to the remainder of the molecule through a heteroatom.

As used herein, the term "alkylene" by itself or as part of another substituent means a divalent radical derived from a branched or unbranched alkane, which may contain one or more heteroatoms as defined herein. Typically, an alkyl (or alkylene) group will have from 1 to 30 carbon atoms, with those groups having 12 or fewer carbon atoms being preferred in the present invention. A "lower alkyl" or "lower alkylene" is a shorter chain alkyl or alkylene group, generally having eight or fewer carbon atoms. In the present context, the term "alkylene" also includes divalent radicals that are linked to the compound via heteroatoms, for example, —OCH$_2$CH$_2$CH$_2$CH$_2$CH$_2$O—.

As used herein, the term "alkenylene" by itself or as part of another substituent means a divalent radical derived from a branched or unbranched alkene, which may contain one or more heteroatoms as defined herein. Typically, an alkenyl (or alkenylene) group will have from 1 to 30 carbon atoms, with those groups having 12 or fewer carbon atoms being preferred in the present invention. A "lower alkenyl" or "lower alkenylene" is a shorter chain alkenyl or alkenylene group, generally having eight or fewer carbon atoms. In the present context, the term "alkenylene" also includes divalent radicals that are linked to the compound via heteroatoms, for example, —OCH=CH$_2$CH$_2$CH=CHO—.

As used herein, the term "alkynylene" by itself or as part of another substituent means a divalent radical derived from a branched or unbranched alkyne, which may contain one or more heteroatoms as defined herein. Typically, an alkynyl (or alkynylene) group will have from 1 to 30 carbon atoms, with those groups having 12 or fewer carbon atoms being preferred in the present invention. A "lower alkynyl" or "lower alkynylene" is a shorter chain alkynyl or alkynylene group, generally having eight or fewer carbon atoms. In the present context, the term "alkenylene" also includes divalent radicals that are linked to the compound via heteroatoms, for example, —OCCCH$_2$CCO—.

As used herein, the term "cycloalkyl" refers to a saturated or unsaturated cyclic hydrocarbon radical comprising from about 3 to about 12 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo, alkylsulfinyl, and nitro. Exemplary cycloalkyl groups include cyclopropyl, cyclobutyl, cyclopentyl, cyclohexyl, cyclohexenyl, cyclohepta-1,3-dienyl, and the like. "Cycloalkyl" is also meant to refer to bicyclic and polycyclic hydrocarbon rings such as, for example, bicyclo[2.2.1]heptane, bicyclo[2.2.2]octane, the like.

As used herein, the term "cycloalkylene" refers to a saturated or unsaturated divalent cyclic hydrocarbon radical comprising from about 3 to about 12 carbon atoms. Cycloalkylene groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo, alkylsulfinyl, and nitro. Exemplary cycloalkyl groups include cyclopropyl, cyclobutyl, cyclopentyl, cyclohexyl, cyclohexenyl, cyclohepta-1,3-dienyl, and the like. "Cycloalkylene" is also meant to refer to bicyclic and polycyclic hydrocarbon rings such as, for example, bicyclo [2.2.1]heptane, bicyclo[2.2.2]octane, the like.

As used herein, the term "heterocyclic ring or group" or "heterocycloalkyl" or "heterocyclyl" refers to a saturated or unsaturated cyclic hydrocarbon group having about 2 to about 12 carbon atoms (preferably about 4 to about 6 carbon atoms) where 1 to about 4 carbon atoms are replaced by one or more nitrogen, oxygen and/or sulfur atoms. Nitrogen and sulfur atoms are optionally oxidized, and the nitrogen atom(s) are optionally quaternized. Sulfur maybe in the thio, sulfinyl or sulfonyl oxidation state. The heterocyclic ring or group can be fused to an aromatic hydrocarbon group. Heterocyclic groups can be unsubstituted or substituted with one, two, three or four substituents independently selected from alkyl, alkoxy, amino, alkylthio, aryloxy, arylthio, arylalkyl, hydroxy, oxo, thial, halo, carboxyl, carboxylic ester, alkylcarboxylic acid, alkylcarboxylic ester, aryl, arylcarboxylic acid, arylcarboxylic ester, amidyl, ester, alkylcarbonyl, arylcarbonyl, alkylsulfinyl, carbomoyl, thiocarbamoyl, sulfonic acid, sulfonic ester, sulfonamido and nitro. Exemplary heterocyclic groups include pyrrolyl, furanyl, thienyl, 3-pyrrolinyl, 4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrhydrofuranyl, tetrazolyl, pynolinyl, pyrrolindinyl, oxazolindinyl 1,3-dioxolanyl, imidazolinyl, imidazolindinyl, pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo (b) thiophenyl, benzimidazolyl, benzothiazolinyl, quinolinyl, and the like.

As used herein, the term "heterocycloalkylene" refers to a saturated or unsaturated cyclic hydrocarbon group having about 2 to about 12 carbon atoms (preferably about 4 to about 6 carbon atoms) where 1 to about 4 carbon atoms are replaced by one or more nitrogen, oxygen and/or sulfur atoms. Nitrogen and sulfur atoms are optionally oxidized, and the nitrogen atom(s) are optionally quaternized. Sulfur maybe in the thio, sulfinyl or sulfonyl oxidation state. The heterocyclic ring or group can be fused to an aromatic hydrocarbon group. Heterocyclic groups can be optionally substituted with one, two, three or four substituents as described above for heterocycloalkyl.

As used herein, the term "heterocyclic compounds" refer to mono- and polycyclic compounds comprising at least one aryl or heterocyclic ring.

As used herein, the term "aryl" means, unless otherwise stated, a polyunsaturated, typically aromatic, hydrocarbon group which can be a single ring or multiple rings (up to three rings) which are fused together or linked covalently. Non-limiting examples of aryl groups include phenyl, pyridyl, napthyl, biphenyl, quinoyl, tetrahydronaphthyl, furanyl, indanyl, indenyl, indoyl, and the like. Aryl groups (including bicyclic aryl groups) can be unsubstituted or substituted with one, two or three substituents independently selected from alkyl, alkoxy, alkylthio, amino, alkylamino, dialkylamino, arylamino, diarylamino, alkylarylamino, halo, cyano, alkylsulfinyl, hydroxy, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, carbomyl, sulfonic acid, sulfonic ester, sulfonamido and nitro. Exemplary substituted aryl groups include tetrafluorophenyl, pentafluorophenyl, sulfonamide, alkylsulfonyl, arylsulfonyl, and the like.

The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, benzopyrazolyl, 5-indolyl, 1-isoquinolyl, 5-isoquinolyl, 2-quinoxalinyl, 5-quinoxalinyl, 3-quinolyl, 6-quinolyl and 1,2,3,4-tetra-hydroquinoline. Substituents for each of the above noted heteroaryl ring systems are selected from the group of acceptable substituents described above in aryl definition section.

As used herein, ther term "arylalkyl" refers to an aryl radical, as defined herein, attached to an alkyl radical, as defined herein. For brevity, the term "aryl" when used in combination with other terms (e.g., aryloxy, arylthioxy, arylalkyl) includes both aryl and heteroaryl rings as defined herein. Non-limiting arylalkyl groups include benzyl, phenylethyl, pyridylmethyl, 4-hydroxybenzyl, 3-fluorobenzyl, 2-fluorophenylethyl, and the like.

As used herein, the term "arylalkenyl" refers to an aryl radical, as defined herein, attached to an alkenyl radical, as defined herein. Non-limiting examples of arylalkenyl groups include styryl, propenylphenyl, and the like.

As used herein, the term "heterocyclicalkyl" or "heteroalkyl" refers to a heterocyclic ring radical, as defined herein, attached to an alkyl radical, as defined herein.

As used herein, the term "alkoxy" refers to $R^{50}O—$, wherein $R^{50}$ is an alkyl group. $R_{50}$ can be a $C_{1-8}$ lower alkyl group. Non-limiting examples of alkoxy groups include methoxy, ethoxy, t-butoxy, cyclopentyloxy, trifluoromethoxy, and the like.

As used herein, the term "aryloxy" refers to $R^{55}O—$, wherein $R^{55}$ is an aryl or heteroaryl group, as defined herein. Non-limiting examples of arylkoxy groups include napthyloxy, quinolyloxy, isoquinolizinyloxy, and the like.

As used herein, the term "alkylthio" refers to $R_{50}S—$, wherein $R_{50}$ is an alkyl group, as defined herein.

As used herein, the term "arylalkoxy" or "alkoxyaryl" refers to an alkoxy group, as defined herein, to which is appended an aryl group, as defined herein. Non-limiting examples include arylalkoxy groups include benzyloxy, phenylethoxy, chlorophenylethoxy, and the like.

As used herein, the term "alkoxyalkyl" refers to an alkoxy group, as defined herein, appended to an alkyl group, as defined herein. Non-limiting examples of alkoxyalkyl groups include methoxymethyl, methoxyethyl, isopropoxymethyl, and the like.

As used herein, the term "cycloalkoxy" refers to $R^{54}O—$, wherein $R^{54}$ is a cycloalkyl group or a bridged cycloalkyl group. Examples of cycloalkoxy groups include cyclopropyloxy, cyclopentyloxy, cyclohexyloxy, norbornyloxy and the like.

As used herein, the term "cycloalkylthio" refers to $R_{54}S—$, wherein $R_{54}$ is a cycloalkyl group or a bridged cycloalkyl group, as defined herein. Non-limiting examples of cycloalkylthio groups include cyclopropylthio, cyclopentylthio, cyclohexylthio, norbonylthio and the like.

As used herein, the term "oxo" refers to —O— or =O.

As used herein, the term "hydroxyalkyl" or "hydroxyaryl" refers to a hydroxy group, appended to an alkyl or an aryl group, as defined herein.

As used herein, the term "halogen" or "halo" refers to iodine (I), bromine (Br), chlorine (Cl), and/or fluorine (F).

As used herein, the term "amino" refers to —$NH_2$, an alkylamino group, a dialkylamino group, an arylamino group, a diarylamino group, an alkylarylamino group, anarylalkylamino group, a heteroaryl or a heterocyclic ring, as defined herein.

As used herein, the term "alkylamino" refers to $R^{50}NH—$, wherein $R^{50}$ is an alkyl group, as defined herein. Non-limiting examples of alkylamino groups include methylamino, ethylamino, butylamino, cyclohexylamino, and the like.

As used herein, the tetra "arylamino" refers to $R^{55}NH—$, wherein $R^{55}$ is an aryl group, as defined herein.

As used herein, the term "dialkylamino" refers to $R_{52}R_{53}N—$, wherein $R_{52}$ and $R_{53}$ are each independently an alkyl group, as defined herein. Exemplary dialkylamino groups include dimethylamino, diethylamino, methyl propargylamino, and the like.

As used herein, the term "diarylamino" refers to $R^{55}R^{60}N—$, wherein $R^{55}$ and $R^{60}$ are each independently an aryl group, as defined herein.

As used herein, the term "alkylarylamino or arylalkylamino" refers to $R^{52}R^{55}N—$, wherein $R^{52}$ is an alkyl group, as defined herein, and $R^{55}$ is an aryl group, as defined herein.

As used herein, the term "alkylarylalkylamino" refers to $R^{52}R^{79}N—$, wherein $R^{52}$ is an alkyl group, as defined herein, and $R^{79}$ is an arylalkyl group.

As used herein, the term "alkylcycloalkylamino" refers to $R^{52}R^{80}N—$, wherein $R^{52}$ is an alkyl group, as defined herein, and $R^{80}$ is an cycloalkyl group, as defined herein.

As used herein, the term "aminoalkyl" refers to an amino group, an alkylamino group, a dialkylamino group, an arylamino group, a diarylamino group, an alkylarylamino group or a heterocyclic ring, as defined herein, to which is appended an alkyl group, as defined herein. Non-limiting examples of aminoalkyl groups include dim ethylaminopropyl, diphenylaminocyclopentyl, methylaminomethyl, and the like.

As used herein, the term "aminoaryl" refers to an aryl group to which is appended an alkylamino group, a arylamino group or an arylalkylamino group. Non-limiting examples of aminoaryl groups include anilino, N-methylanilino, N-benzylanilino, and the like.

As used herein, the term "thio" refers to —S— or —SH.

As used herein, the term "sulfonyl" refers to —S(O)—.

As used herein, the term "sulfonyl" refers to —$S(O)_2$—.

As used herein, the term "sulfonate" refers to —O—$S(O)_2$—O—, $R^{50}O—S(O)_2—O—$ or $R^{55}—O—S(O)_2—O—$, where $R^{50}$ is an alkyl group and $R^{55}$ is an aryl group, as defined herein.

As used herein, the term "sulfonamido" refers to —$S(O)_2$—$N(R^{51})(R^{57})$, wherein $R^{51}$ and $R^{57}$ are each independently a hydrogen atom, an alkyl group, an aryl group or an heteroaryl, as defined herein, or $R^{51}$ and $R^{57}$ when taken together are a heterocyclic ring, a cycloalkyl group or a bridged cycloalkyl group, as defined herein.

As used herein, the term "alkylsulfonamido" refers to a sulfonamido group, as defined herein, appended to an alkyl group, as defined herein.

As used herein, the term "arylsulfonamido" refers to a sulfonamido group, as defined herein, appended to an aryl group, as defined herein.

As used herein, the term "alkylthio" refers to $R^{50}S-$, wherein $R^{50}$ is an alkyl group, as defined herein (preferably a lower alkyl group, as defined herein).

As used herein, the term "arylthio" refers to $R^{55}S-$, wherein $R^{55}$ is an aryl group, as defined herein.

As used herein, the term "arylalkylthio" refers to an aryl group, as defined herein, appended to an alkylthio group, as defined herein.

As used herein, the term "alkylsulfinyl" refers to $R^{50}-S(O)-$, wherein $R^{50}$ is an alkyl group, as defined herein.

As used herein, the term "alkylsulfonyl" refers to $R^{50}-S(O)_2-$, wherein $R^{50}$ is an alkyl group, as defined herein.

As used herein, the term "alkylsulfonyloxy" refers to $R^{50}-S(O)_2-O-$, wherein $R^{50}$ is an alkyl group, as defined herein.

As used herein, the term "arylsulfinyl" refers to $R^{55}-S(O)_2-$, wherein $R^{55}$ is an aryl group, as defined herein.

As used herein, the term "arylsulfonyl" refers to $R^{55}-S(O)_2-$, wherein $R^{55}$ is an aryl group, as defined herein.

As used herein, the term "arylsulfonyloxy" refers to $R^{55}-S(O)_2-O-$, wherein $R^{55}$ is an aryl group, as defined herein.

As used herein, the term "amidyl" refers to $R^{51}C(O)N(R^{57})-$, wherein $R^{51}$ and $R^{57}$ are each independently a hydrogen atom, an alkyl group, an aryl group, a cycloalkyl, a heteroalkyl, a heterocycloalkyl or a heteroaryl, as defined herein.

As used herein, the term "carbamoyl" refers to $-C(O)N(R^{51})(R^{57})$, wherein $R^{51}$ and $R^{57}$ are each independently a hydrogen atom, an alkyl group, a cycloalkyl, an aryl group, a heteroalkyl, a heterocycloalkyl or an heteroaryl ring, as defined herein, or $R^{51}$ and $R^{57}$ taken together are a heterocyclic ring or a bridged cycloalkyl group, as defined herein.

As used herein, the term "thiocarbamoyl" refers to $-C(S)N(R^{51})(R^{57})$, wherein $R^{51}$ and $R^{57}$ are each independently a hydrogen atom, an alkyl group, a cycloalkyl, an aryl group, a heteroalkyl, a heterocycloalkyl or an heteroaryl ring, as defined herein, or $R^{51}$ and $R^{57}$ taken together are a heterocyclic ring or a bridged cycloalkyl group, as defined herein.

As used herein, the term, "carbamoyl-oxy" refers to $-OC(O)N(R^{51})(R^{57})$ and the term "carbamoyl-amino" refers to $-N(R^{61})C(O)N(R^{51})(R^{57})$, wherein $R^{51}$, $R^{57}$ and $R^{61}$ are each independently a hydrogen atom, an alkyl group, a cycloalkyl, an aryl group, a heteroalkyl, a heterocycloalkyl or an heteroaryl ring, as defined herein, or $R^{51}$ and $R^{57}$ taken together are a heterocyclic ring or a bridged cycloalkyl group, as defined herein.

As used herein, the term, "thiocarbamoyl-oxy" refers to $-OC(S)N(R^{51})(R^{57})$ and the term "thiocarbamoyl-amino" refers to $-N(R^{61})C(S)N(R^{51})(R^{57})$, wherein $R^{51}$, $R^{57}$ and $R^{61}$ are each independently a hydrogen atom, an alkyl group, a cycloalkyl, an aryl group, a heteroalkyl, a heterocycloalkyl or an heteroaryl ring, as defined herein, or $R^{51}$ and $R^{57}$ taken together are a heterocyclic ring or a bridged cycloalkyl group, as defined herein.

As used herein, the term, "carboxyl" refers to $R^{76}(O)CO-$, wherein $R^{76}$ is a hydrogen atom, an alkyl group, a cycloalkyl, an aryl group, a heteroalkyl, a heterocycloalkyl or an heteroaryl ring, as defined herein.

As used herein, the term, "alkanoyl" refers to $R^{52}-C(O)-$, wherein $R^{52}$ is an alkyl group, a heteroalkyl, a cycloalkyl, a heterocycloalkyl group, as defined herein.

As used herein, the "aroyl" refers to $R^{55}-C(O)-$, wherein $R^{55}$ is an aryl group, an heteroaryl group, as defined herein.

As used herein, the term, "alkoxycarbonyl" refers to $-C(O)OR^{52}$, wherein $R^{52}$ is H, an alkyl group, a cycloalkyl, a heteroalkyl, an arylalkyl, a heteroarylalkyl, as defined herein.

As used herein, the term, "aryloxycarbonyl" refers to $-C(O)OR^{56}$, wherein $R^{56}$ is an aryl or a heteroaryl as defined herein.

As used herein, the term, "alkylcarboxylic ester" refers to an alkyl group, as defined herein, appended to a carboxylic ester group, as defined herein.

As used herein, the term, "arylcarboxylic acid" refers to an aryl group, as defined herein, appended to a carboxyl group, as defined herein.

As used herein, the term, "arylcarboxylic ester" and "arylcarboxyl" refer to an aryl group, as defined herein, appended to a carboxylic ester group, as defined herein.

As used herein, the term, "ureido" refers to $-N(R^{59})C(O)N(R^{51})(R^{57})$, wherein $R^{51}$ $R^{57}$ and $R^{59}$ are each independently a hydrogen atom, an alkyl group, a cycloalkyl, an aryl group, a heteroalkyl, a heterocycloalkyl or an heteroaryl ring, as defined herein, or $R^{51}$ and $R^{57}$ taken together are a heterocyclic ring or a bridged cycloalkyl group, as defined herein.

As used herein, the term, "thioureido" refers to $-N(R^{59})C(S)N(R^{51})(R^{57})$, wherein $R^{51}$ $R^{57}$ and $R^{59}$ are each independently a hydrogen atom, an alkyl group, a cycloalkyl, an aryl group, a heteroalkyl, a heterocycloalkyl or an heteroaryl ring, as defined herein, or $R^{51}$, and $R^{57}$ taken together are a heterocyclic ring or a bridged cycloalkyl group, as defined herein.

As used herein, the term, "silyl" refers to $-Si(R^{73})(R^{74})(R^{75})$, wherein $R^{73}$, $R^{74}$ and $R^{75}$ are each independently a covalent bond, H, a lower alkyl, a heteroalkyl, an alkoxy, an aryl, an aryloxy, a heteroaryl, an arylalkoxy, a halide or a carboxyl, as defined herein.

As used herein, the terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-12 membered ring with the nitrogen atom to which each is attached. Accordingly, a group represented as $-NR'''R''$ is meant to include piperidinyl, pyrrolidinyl, morpholinyl, azetidinyl and the like.

As used herein, the terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

As used herein, the term "arylene" by itself or as part of another substituent means a divalent radical derived from a polyunsaturated, typically aromatic, hydrocarbon group which can be a single ring or multiple rings (up to three rings) which are fused together or linked covalently. Optionally, the aromatic ring(s) can have one or more hetero atoms. Typically, an aryl (or arylene) group will have from 1 to 30 carbon atoms, with those groups having 12 or fewer carbon atoms being preferred in the present invention.

As used herein, the terms "triarylene" and "tetraarylene" mean a trivalent and tetravalent radicals, respectively derived from a polyunsaturated, typically aromatic, hydrocarbon group which can be a single ring or multiple rings (up to three rings) which are fused together or linked covalently. Optionally, the aromatic ring(s) can have one or more hetero atoms. Typically, an triaryl (or triarylene) group will have from 1 to 30 carbon atoms, with those groups having 12 or fewer carbon atoms being preferred in the present invention.

Substituents for the alkyl radicals (including those groups often referred to as alkylene, alkenyl, alkynyl and cycloalkyl) can be a variety of groups selected from: -halogen, —OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2m'+1), where m' is the total number of carbon atoms in such radical. R', R" and R'" each independently refer to hydrogen, unsubstituted C$_{1-8}$ alkyl, unsubstituted heteroalkyl, unsubstituted aryl, aryl substituted with 1-3 halogens, unsubstituted C$_{1-8}$ alkyl, C$_{1-8}$ alkoxy or C$_{1-8}$ thioalkoxy groups, or unsubstituted aryl-C$_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro(C$_1$-C$_8$)alkoxy, and perfluoro(C$_1$-C$_8$)alkyl, in a number ranging from zero to the total number of open valences on the aromatic ring system; and where R', R" and R'" are independently selected from hydrogen, C$_{1-8}$ alkyl, C$_{3-6}$ cycloalkyl, C$_{2-8}$ alkenyl, C$_{2-8}$ alkynyl, unsubstituted aryl and heteroaryl, (unsubstituted aryl)-C$_{1-8}$ alkyl, and unsubstituted aryloxy-C$_{1-8}$ alkyl. Other suitable substituents include each of the above aryl substituents attached to a ring atom by an alkylene tether of from 1-8 carbon atoms.

As used herein, the term "dendritic unit" or "branched unit" refers to a structural unit of the poly(amino ester)s that is covalently bonded to the polymer backbone via at least three covalent bonds, thereby causing a branching of the polymer backbone. A branched unit of present invention can have a structure defined by the above formulae. As also used herein, the term "dendritic" or "branched" or "hyperbranched" is interchangeable and refers to a branched polymer in which one branch of a polymeric backbone has at least one other branch. The dendritic unit can have an exemplified structure shown below:

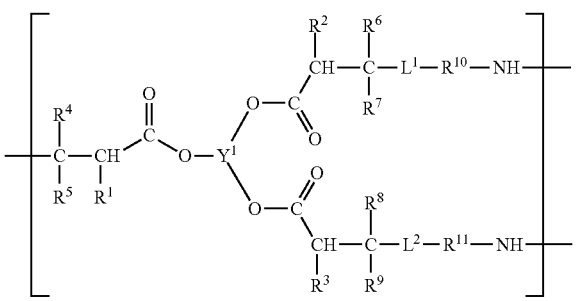

As used herein, the term "branch point" refers to a point in a polymer in which one polymer backbone or branch (comprising a plurality of reacted monomers) is covalently coupled to two or more other polymer backbones or branches (comprising a plurality of reacted monomers).

As used herein, the term "acrylate" or "acrylate monomer" refers to a molecule containing at least one acrylate functionality that has a carbon-carbon double bond in conjugation with a carbonyl group of the acrylate. As used herein, the term "acrylate" also refers to a structural motif containing at least one acrylate functionality that has a carbon-carbon double bond in conjugation with a carbonyl group of the acrylate.

As used herein, the term "triacrylate" or "tris(acrylate ester)" or "triacrylate ester" is used interchangeably and refers to an acrylate monomer having three acrylate functionalities attached to a common structure.

As used herein, the term "tetraacrylate" or "tetrakis(acrylate ester)" or "tetraacrylate ester" is used interchangeably and refers to an acrylate monomer having four acrylate functionalities attached to a common structure.

As used herein, the term "ester linkage(s)" refers to a structural unit having the formula —OC(O)—CH(R$^{70}$)— in the polymer backone, wherein R$^{70}$ is H, hydroxyl, thiohydroxyl or hydrocarbyl, as defined herein.

As used herein, the term "linear unit" refers to a structural unit of the poly(amino ester)s that is covalently bonded to the polymer backbone via two covalent bonds, thereby extending the polymer backbone in a substantially linear manner. The linear unit can have an exemplified structure shown below:

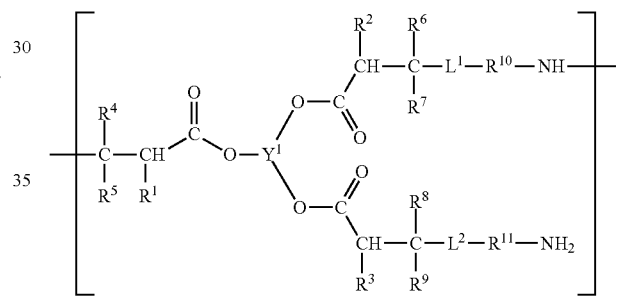

As used herein, the term "terminal unit" refers to a structural unit of the poly(amino ester)s that occurs at the end or terminus of a polymer chain. The terminal unit can have an exemplified structure shown below:

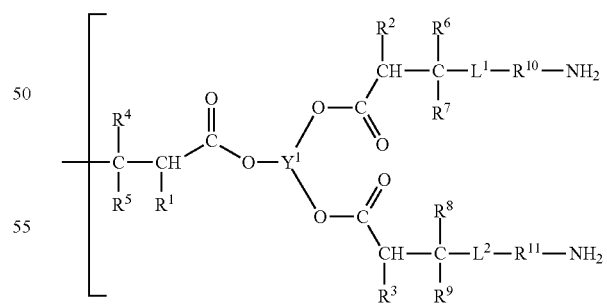

A used herein, the term "diamine monomer" refers to compounds having one secondary amino group and one primary amino group. The compounds can further comprise one or more tertiary amino groups.

As used herein, the term "acrylate monomer" refers to compounds containing at least one acrylate functionality/moiety or acrylate-like functionality/moiety. An acrylate functionality has a carbon-carbon double bond in conjugation with a carbonyl or an ester group/moiety. Preferably, an acrylate monomer has 3, 4, 5 or 6 acrylate functionalities.

As used herein, the term "therapeutically effective amount" refers to an amount effective, at dosages and for periods of time necessary, to achieve the desired therapeutic result. A therapeutically effective amount of any particular therapeutic agent may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects.

As used herein, the term, a "prophylactically effective amount" refers to an amount effective, at dosages and for periods of time necessary, to achieve a desired prophylactic result, such as preventing or inhibiting the rate of various disease onsets or progressions. A prophylactically effective amount can be determined as described above for the therapeutically effective amount. For any particular subject, specific dosage regimens may be adjusted over time according to the individual need and the professional judgment of the person administering or supervising the administration of the compositions.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such pharmaceutically acceptable carriers and excipients for pharmaceutically active substances is well known in the art. Except insofar as any conventional pharmaceutically acceptable carriers and excipients is incompatible with the active compound, use thereof in the pharmaceutical compositions of present invention is contemplated. Supplementary active compounds can also be incorporated into the compositions.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

GENERAL

The present invention provides branched poly(amino ester)s having ester or ester-like linkages between two optionally substituted nitrogen units. In one aspect, the compounds have a dendritic polymer backbone structure comprising at least one secondary amine linkage and at least one tertiary amine linkage. The hyperbranched or dendritic poly(amino ester)s can be prepared using addition polymerization reactions. The present invention also provides application of the compounds in the treatment and diagnosis of diseases. Advantageously, the branched poly(amino ester)s of the present invention have a higher concentration of secondary and tertiary amino groups, low cytotoxicity, good biocompatibility and biodegradability, superior transfection efficiency and high solubility as compared to other polymers, such as PEIs. The globular-like structures of the dentritic or hyperbranched poly(amino ester)s also offer unique advantage of having higher density of amine and ester functional linkages, which are important for achieving good biodegradability and high cell transfection efficiency.

In one aspect, the biodegradable poly(amino ester) of the present invention can be prepared by a Michael addition reaction of an acrylate monomer comprising at least three acrylate functionalities with a diamine monomer, wherein the diamine monomer has one primary amino group and one secondary amino group. The properties, such as the degree of branching of the biodegradable compounds can be regulated by varying the feed ratio of the acrylate and the diamine monomers. To enhance the stability and/or to further functionalize the polymers, the branched poly(amino ester)s can also be end-capped by reacting with a suitable end-capping agent. Advantageously, the method is easy to operate and gives the desired compounds in high yield.

In another aspect, the present invention provides pharmaceutical compositions and compositions for transfecting cells. The compositions can be used in treating disease, or as vectors in gene therapy. In a different aspect, the dendritic or hyperbranched poly(amino ester) compounds of the present invention is unexpectedly found to exhibit strong fluorescence property when excited by UV light. The present invention also contemplates compositions that are useful for preparing biocompatible imaging agents.

COMPOUNDS

The present invention provides a branched poly(amino ester) compound having a polymer backbone comprising at least one secondary amine linkage and at least one tertiary amine linkage. More particularly, the branched poly(amino ester) compound has a ester or ester-like linkage between two optionally substituted nitrogen units.

In one aspect, the present invention provides a branched poly(amino ester) compound having the formula:

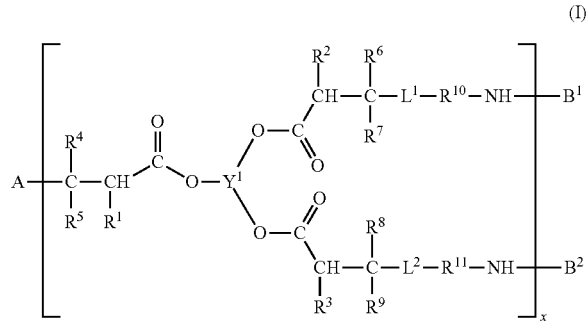

(I)

In the above formula (I), subscript x is an integer between 1 and about 10,000. Preferably, x is between 1 and 2000. In one embodiment, x is 1. In some embodiments, the compounds have a polydispersity index from about 1 to about 10, 1 to 3, 2 to 4, 1 to 5, 2 to 6, 3 to 7 or 6 to 10. Preferably, the polydispersity index is from about 1 to about 5, such as about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 or 5.0. In another embodiment, the compound has a polydispersity index close to 1. Polydispersity index is a measure of the polydispersity of the polymers prepared. A narrow polydispersity index is an indication that all the polymers in the sample have the similar chain length or number of repeat units. For example, a pure sample containing molecules of the same size and/or molecular weight has a polydispersity index equivalent to 1.

Each of $R^1$, $R^2$ and $R^3$ is independently selected from the group consisting of hydrogen, deuterium, tritium, hydroxyl, thiohydroxyl and hydrocarbyl. In some preferred embodiments, each of $R^1$, $R^2$ and $R^3$ is hydrogen, deuterium, or hydrocarbyl. Preferably, the hydrocarbyl is $C_{1-8}$alkyl or $C_{1-8}$heteroalkyl. In other more preferred embodiments, each of $R^1$, $R^2$ and $R^3$ is independently hydrogen, deuterium or $CH_3$. In even more preferred embodiments, $R^1$, $R^2$ and $R^3$ are hydrogen or deuterium.

Each of $R^4$, $R^5$, $R^6$, $R^7$, $R^8$ and $R^9$ is independently hydrogen, deuterium, tritium, or hydrocarbyl. In a preferred embodiment, two of $R^4$, $R^5$, $R^6$, $R^7$, $R^8$ and $R^9$ are hydrogen, deuterium, tritium. In another preferred embodiment, three of $R^4$, $R^5$, $R^6$, $R^7$, $R^8$ and $R^9$ are hydrogen, deuterium, tritium. In yet another preferred embodiment, four of $R^4$, $R^5$, $R^6$, $R^7$, $R^8$ and $R^9$ are hydrogen, deuterium, tritium. In still another preferred embodiment, five of $R^4$, $R^5$, $R^6$, $R^7$, $R^8$ and $R^9$ are hydrogen, deuterium, tritium. In the most preferred embodiment, $R^4$, $R^5$, $R^6$, $R^7$, $R^8$ and $R^9$ are hydrogen or deuterium.

$L^1$ and $L^2$ are divalent linking groups. Each of $L^1$ and $L^2$ is independently selected from the group consisting of $NR^{12}$ and $N(—R^{13}—)(—R^{14}—)Z$, wherein each of $R^{13}$ and $R^{14}$ is bonded to N and Z to form a cyclic structure. In some embodiments, $L^1$ and $L^2$ are $NR^{12}$. In yet other embodiments, $L^1$ is $NR^{12}$ and $L^2$ is $N(—R^{13}—)(—R^{14}—)Z$; or $L^2$ is $NR^{12}$ and $L^1$ is $N(—R^{13}—)(—R^{14}—)Z$. In still other embodiments, $L^1$ and $L^2$ are $N(—R^{13}—)(—R^{14}—)Z$.

$R^{12}$ can be independently H, hydrocarbyl, hydroxyl or thiohydroxyl. In some preferred embodiments, $R^{12}$ is H, hydrocarbyl or hydroxyl: In some more preferred embodiments, $R^{12}$ is H, $C_{1-8}$alkyl, $C_{1-8}$cycloalkyl, $C_{1-8}$heteroalkyl, aryl and heteroaryl.

Each of $R^{10}$, $R^{11}$, $R^{13}$ and $R^{14}$ can be independently oxo, —S—, optionally substituted $C_{1-30}$alkylene, optionally substituted $C_{2-30}$ alkenylene, optionally substituted $C_{2-30}$ alkynylene, optionally substituted $C_{3-8}$ cycloalkylene or optionally substituted $C_{6-18}$arylene, any of which may optionally contain one or more heteroatoms selected from the group consisting of N, O and S. In some preferred embodiments, $R^{10}$, $R^{11}$, $R^{13}$ and $R^{14}$ can be optionally substituted $C_{1-30}$ alkylene, optionally substituted $C_{3-8}$ cycloalkylene or optionally substituted $C_{6-18}$ arylene. More preferably, $R^{10}$, $R^{11}$, $R^{13}$ and $R^{14}$ are optionally substituted $C_{1-30}$ alkylene, for example, $CH_2$—$CH_2$.

Each Z is independently selected from the group consisting of N, CH, C-hydrocarbyl, trialkyl, triarylene, tris-N,N-dialkylamino, tris-N,N-diarylamino, tris-N-alkyl, N-arylamino, silyl, a metal and $C(R^aR^b)$, wherein each $R^a$ and $R^b$ is independently a bond, H or hydrocarbyl or together with C join to form a four- to twelve-member carbocyclic or heterocyclic ring, preferably that $R^1$, $R^2$, $R^3$, $R^4$, $R^5$, $R^6$, $R^7$, $R^8$, $R^9$ and $R^{12}$ do not have a primary amino group, a secondary amino group, or a carbon-carbon double bond conjugated to a carbonyl group. The C-hydrocarbyl can be $CC_{1-8}$alkyl, C-cycloalkyl, C-heteroalkyl, C-aryl or C-heteroaryl. Triarylene includes triphenylene and the like. Tris-N,N-dialkylamino, tris-N,N'-diarylamino and tris-N-alkyl, N-arylamino have the formula $[NR^{ak}]_3R^k$, wherein each of $R^{ak}$ and $R^k$ is independently alkyl, cycloalkyl or aryl. $R^{ak}$ is preferably a $C_{1-8}$alkyl, $C_{1-8}$cycloalkyl, $C_{6-10}$aryl or $C_{6-10}$arylalkyl. Silyl groups can be SiH. Arylsilyl, arylalkylsilyl or alkylsily. The metal can be main group metal, such as B, Al, Ga, In or Tl; or transitional metal, such as Fe, Ru, Cr, V, Ta or Au. In some preferred embodiments, Z is N, CH, CC$_{1-8}$alkyl, SiH, SiC$_{1-8}$alkyl or a metal selected from the group consisting of B, Al, Ga and In.

Symbol Y$^1$ is selected from the group consisting of N, CH, C-hydrocarbyl, trialkyl, triarylene, heteroarylene, tricycloalkylene, triheterocycloalkylene, tris-N,N-dialkylamino, tris-N,N-diarylamino, silyl and a metal. Preferred C-hydrocarbyl includes, but not limited to CH, CR$^d$, wherein R$^d$ is C$_{1-12}$alkyl, C$_{1-8}$cycloalkyl, C$_{1-8}$heteroalkyl, C$_{6-10}$aryl and C$_{4-6}$heteroaryl. Preferred trialkyl includes R$^e$(R$^f$—)$_3$, wherein R$^e$ is N, aryl, heteroaryl, C$_{1-8}$alkyl or C$_{3-8}$cycloalkyl; R$^f$ is a bond, C$_{1-30}$alkyl or C$_{1-30}$arylalkyl. R$^f$ is preferred to have 0 to 8 carbons. Silyl groups can be SiR$^g$, wherein R$^g$ is H, C$_{1-8}$alkyl, C$_{1-8}$heteroalkyl, arylalkyl, aryl or heteroaryl. The metal used can be Fe, Al, Ga, B, In and the like. In some preferred embodiments, Y$^1$ is N, CH, (CH$_2$)$_3$C(CH$_2$CH$_3$), (CH$_2$)$_3$N or (CH$_2$)$_3$Si(CH$_2$CH$_3$).

Symbols A, B$^1$ and B$^2$ in formula (I) represent end-groups. End-groups are functional groups located at the prephery of the dendritic polymer structures. Preferably "A" group is a nucleophile. Each A is independently selected from the group consisting of H, NH$_2$, hydrocarbyl, hydroxyl, carboxyl, thio, amidyl, alkylthio, aryloxy, alkylamino, arylamino, heterocyclyl, heteroaryl, dialkylamino and diarylamino. Preferred end-groups include, but are not limited to, alkylamino, dialkylamino, diarylamino, morpholinyl, optionally substituted piperazinyl, optionally substituted piperidinyl, optionally substituted azetidinyl and optionally substituted pyrrolidinyl. More preferred end-groups include morpholinyl, N-methyl piperazinyl, N-ethyl piperazinyl, dimethylamino, diethylamino, and 1-methyl-4-methylamino-piperidinyl, benzyl-1-piperazinyl carboxylate.

Symbols B$^1$ and B$^2$ in formula (I) represent end-groups. Preferred B$^1$ and B$^2$ are each independently an electrophile. Each of B$^1$ and B$^2$ can be independently H, hydroxyl or hydrocarbyl. Suitable agents that can form end-groups B$^1$ and B$^2$ include, but are not limited to, acrylates, acrylamides, acrylic acids, alkanoyl halides, alkenyl halides, aryl halide, heteroaryl halide, arylalkyl halides, aldehyde, keones, tosyl halides, mesyl halides, alkyl halides, heteroalkyl halide, carboxylic acids, carboxylic acid anhydrides and isocyanates.

In some preferred embodiments, present invention provides compounds having the formula (Ia):

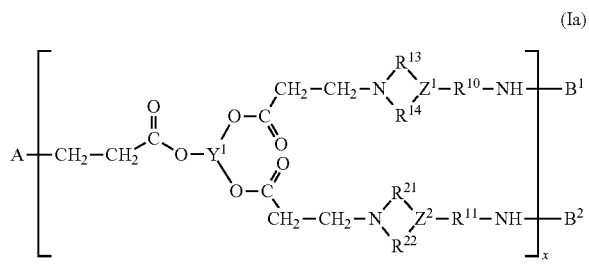

(Ia)

In formula (Ia), x is an integer from 1 to about 2000. Y$^1$ is CH, C—(C$_{1-8}$alkyl), C—(C$_{1-8}$heteroalkyl), C—(C$_{7-12}$arylalkyl), C—(C$_{6-10}$aryl), C—(C$_{4-6}$heteroaryl), SiH, Si—(C$_{1-8}$alkyl), Si—(C$_{1-8}$heteroalkyl), Si—(C$_{6-10}$aryl), Si—(C$_{4-6}$heteroaryl) or a metal, such as B or Al. R$^{10}$, R$^{11}$, R$^{13}$, R$^{14}$, R$^{21}$ and R$^{22}$ are each independently C$_{1-8}$alkylene; preferably CH$_2$CH$_2$. Z$^1$ and Z$^2$ are each independently N, CH, C—(C$_{1-8}$alkyl), C—(C$_{1-8}$heteroalkyl), C—(C$_{7-12}$arylalkyl), C—(C$_{6-10}$aryl), C—(C$_{4-6}$heteroaryl), SiH, Si—(C$_{1-8}$alkyl), Si—(C$_{1-8}$heteroalkyl), Si—(C$_{6-10}$aryl), Si—(C$_{4-6}$heteroaryl) or a metal, such as B or Al. Preferably, end-group "A" includes, but is not limited to, H, NH$_2$, C$_{1-8}$alkyl, hydroxyl, carboxyl, amidyl, alkykoxy, aryloxy, heteroaryloxy, alkylamino, arylamino, dialkylamino and diarylamino. More preferably end-group "A" includes, but is not limited to, C$_{1-8}$alkylamino, diC$_{1-8}$alkylamino, C$_{6-10}$arylamino, diC$_{6-10}$arylamino, C$_{1-8}$alkylC$_{6-10}$arylamino, morpholinyl, optionally substituted piperazinyl, optionally substituted piperidinyl, optionally substituted azetidinyl and optionally substituted pyrrolidinyl, morpholinyl, N-methyl piperazinyl, N-ethyl piperazinyl, and 1-methyl-4-methylamino-piperidinyl, benzyl-1-piperazinyl carboxylate. Preferred agents that can form independent end-groups B$^1$ and B$^2$ include, but are not limited to, acrylates, acrylamides, acrylic acids, alkanoyl halides, alkenyl halides, aryl halide, heteroaryl halide, arylalkyl halides, aldehyde, keones, tosyl halides, mesyl halides, alkyl halides, heteroalkyl halide, carboxylic acids, carboxylic acid anhydrides and isocyanates.

In another aspect, the present invention provides a branched poly(amino ester) compound having the formula:

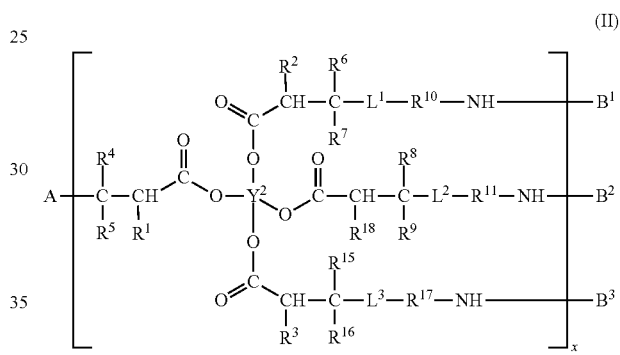

(II)

In the above formula (II), subscript x is an integer between 1 and about 10,000. Preferably, x is between 1 and 2000. In one embodiment, x is 1. In some embodiments, the compounds have a polydispersity index from about 1 to about 10, 1 to 3, 2 to 4, 1 to 5, 2 to 6, 3 to 7 or 6 to 10. Preferably, the polydispersity index is from about 1 to about 6, such as about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0. In another embodiment, the compound has a polydispersity index close to 1.

Each of R$^1$, R$^2$, R$^3$ and R$^{18}$ is independently selected from the group consisting of hydrogen, deuterium, tritium, hydroxyl, thiohydroxyl and hydrocarbyl. In some preferred embodiments, each of R$^1$, R$^2$, R$^3$ and R$^{18}$ is hydrogen, deuterium, or hydrocarbyl. Preferably, the hydrocarbyl is C$_{1-8}$alkyl or C$_{1-8}$heteroalkyl. In a more preferred embodiments, each of R$^1$, R$^2$, R$^3$ and R$^{18}$ is independently hydrogen, deuterium or CH$_3$. In an even more preferred embodiment, R$^1$, R$^2$, R$^3$ and R$^{18}$ are hydrogen or deuterium.

Each of R$^4$, R$^5$, R$^6$, R$^7$, R$^8$, R$^9$, R$^{15}$ and R$^{16}$ is independently hydrogen, deuterium, tritium, or hydrocarbyl. In a preferred embodiment, two of R$^4$, R$^5$, R$^6$, R$^7$, R$^8$, R$^9$, R$^{15}$ and R$^{16}$ are hydrogen, deuterium, tritium. In another preferred embodiment, three of R$^4$, R$^5$, R$^6$, R$^7$, R$^8$, R$^9$, R$^{15}$ and R$^{16}$ are hydrogen, deuterium, tritium. In yet another preferred embodiment, four of R$^4$, R$^5$, R$^6$, R$^7$, R$^8$, R$^9$, R$^{15}$ and R$^{16}$ are hydrogen, deuterium, tritium. In still another preferred embodiment, five of R$^4$, R$^5$, R$^6$, R$^7$, R$^8$, R$^9$, R$^{15}$ and R$^{16}$ are hydrogen, deuterium, tritium. In yet a further preferred embodiment, six of $R^4$, $R^5$, $R^6$, $R^7$, $R^8$, $R^9$, $R^{15}$ and $R^{16}$ are hydrogen, deuterium, tritium. In still a further preferred embodiment, seven of $R^4$, $R^5$, $R^6$, $R^7$, $R^8$, $R^9$, $R^{15}$ and $R^{16}$ are hydrogen, deuterium, tritium. In the most preferred embodiment, $R^4$, $R^5$, $R^6$, $R^7$, $R^8$, $R^9$, $R^{15}$ and $R^{16}$ are hydrogen or deuterium.

$L^1$, $L^2$ and $L^3$ are linking groups. Each of $L^1$, $L^2$ and $L^3$ is independently selected from the group consisting of $NR^{12}$ and $N(-R^{13}-)(-R^{14}-)Z$, each of $R^{13}$ and $R^{14}$ is bonded to N and Z to form a cyclic structure. In some embodiments, $L^1$, $L^2$ and $L^3$ are $NR^{12}$. In other embodiments, $L^1$, $L^2$ and $L^3$ are $N(-R^{13}-)(-R^{14}-)Z$. In still other embodiments, any two of the linkages from $L^1$, $L^2$ and $L^3$ can be different from the third. For example, $L^1$ and $L^2$ are $NR^{12}$, $L^3$ is $N(-R^{13}-)(-R^{14}-)Z$; or $L^2$ and $L^3$ are $NR^{12}$, $L^1$ is $N(-R^{13}-)(-R^{14}-)Z$; or $L^1$ and $L^3$ are $NR^{12}$, $L^2$ is $N(-R^{13}-)(-R^{14}-)Z$; or $L^1$ is $NR^{12}$, $L^2$ and $L^3$ are $N(-R^{13}-)(-R^{14}-)Z$; or $L^2$ is $NR^{12}$, $L^1$ and $L^3$ are $N(-R^{13}-)(-R^{14}-)Z$; or $L^1$ and $L^2$ are $N(-R^{13}-)(-R^{14}-)Z$.

$R^{12}$ can be independently H, hydrocarbyl, hydroxyl or thiohydroxyl. In some preferred embodiments, $R^{12}$ is H, hydrocarbyl or hydroxyl. In some more preferred embodiments, $R^{12}$ is H, $C_{1-8}$alkyl, $C_{1-8}$cycloalkyl, $C_{1-8}$heteroalkyl, aryl and heteroaryl.

Each of $R^{10}$, $R^{11}$, $R^{13}$, $R^{14}$ and $R^{17}$ is independently oxo, —S—, optionally substituted $C_{1-30}$ alkylene, optionally substituted $C_{2-30}$ alkenylene; optionally substituted $C_{2-30}$ alkynylene, optionally substituted $C_{3-8}$ cycloalkylene or optionally substituted $C_{6-18}$ arylene, any of which may optionally contain one or more heteroatoms selected from the group consisting of N, O and S. In some preferred embodiments, each of $R^{10}$, $R^{11}$, $R^{13}$, $R^{14}$ and $R^{17}$ can be independently optionally substituted $C_{1-30}$ alkylene, optionally substituted $C_{3-8}$ cycloalkylene or optionally substituted $C_{6-18}$ arylene. More preferably, each of $R^{10}$, $R^{11}$, $R^{13}$, $R^{14}$ and $R^{17}$ is optionally substituted $C_{1-30}$alkylene. Most preferably, $R^{10}$, $R^{11}$, $R^{13}$, $R^{14}$ and $R^{17}$ are $CH_2CH_2$.

In formula (II), each Z is independently selected from the group consisting of N, CH, C-hydrocarbyl, trialkyl, triarylene, heteroarylene, tricycloalkylene, triheterocycloalkylene, tris-N,N-dialkylamino, tris-N,N-diarylamino, tris-N-alkyl, N-arylamino, silyl, a metal and $C(R^aR^b)$, wherein each $R^a$ and $R^b$ is independently a bond, H or hydrocarbyl or together with C join to form a four- to twelve-member carbocyclic or heterocyclic ring, preferably that $R^1$, $R^2$, $R^3$, $R^4$, $R^5$, $R^6$, $R^7$, $R^8$, $R^9$ and $R^{12}$ do not have a primary amino group, a secondary amino group, or a carbon-carbon double bond conjugated to a carbonyl group. The C-hydrocarbyl can be $CC_{1-8}$alkyl, C-cycloalkyl, C-heteroalkyl, C-aryl or C-heteroaryl. Triarylene includes triphenylene and the like. Tris-N,N-dialkylamino, tris-N,N-diarylamino and tris-N-alkyl, N-arylamino have the formula $[NR^{ak}]_3R^k$, wherein each of $R^{ak}$ and $R^k$ is independently alkyl, cycloalkyl or aryl. $R^{ak}$ is preferably a $C_{1-8}$alkyl, $C_{1-8}$cycloalkyl, $C_{6-10}$aryl or $C_{6-10}$arylalkyl. Silyl groups can be SiH. Arylsilyl, arylalkylsilyl or alkylsily. The metal can be main group metal, such as B, Al, Ga, In or Tl; or transitional metal, such as Fe, Ru, Cr, V, Ta or Au. In some preferred embodiments, Z is N, CH, $CC_{1-8}$alkyl, SiH, $SiC_{1-8}$alkyl or a metal selected from the group consisting of B, Al, Ga and In. In some even more preferred embodiments, each of $R^{10}$, $R^{11}$, $R^{13}$, $R^{14}$, $R^{17}$ is independently $CH_2CH_2$ and Z is CH or N $Y^2$ is selected from the group consisting of C, silyl, tetralkyl, tetraaryl, tetraarylene, tetraheteroalkylene, tetracycloalkylene, tetraheterocycloalkylene, tetraheteroarylene, tetra-N,N-dialkylamino, tetra-N,N-diarylamino, tetraheteroalkylene, tetracycloalkylene, heteroarylene, and a metal.

Preferred tetraalkyl includes $R^h(R^i-)_4$, wherein $R^h$ is C, Si, aryl, or $C_{4-8}$tetracycloalkyl. $R^i$ can be H, $C_{1-30}$alkylene or $C_{1-30}$arylalkylene. Preferred tetraaryl includes $R^h(Ar^1-)_4$, wherein $Ar^1$ is arylene or heteroarylene. Preferably, $Ar^1$ is $C_{6-10}$arylene, $C_{8-12}$arylalkylene or $C_{4-6}$heteroarylene. The metal used can be Ti, Zr, Mn, Ge, Sn and the like. In some preferred embodiments, $Y^2$ is C, Si, $(C_{1-30}$alkylene$)_4C$, $(C_{8-12}$arylalkylene$)_4C$ or $(C_{1-30}$alkylene$)_4Si$. In some more preferred embodiments, $Y^2$ is $(C_{1-8}$alkylene$)_4C$, $(C_{8-12}$arylalkylene$)_4C$ or $(C_{1-8}$alkylene$)_4Si$. In particular preferred embodiments, $Y^2$ is $(CH_2)_4C$, $(CH_2C_6H_4CH_2)_4C$ or $(CH_2)_4Si$.

Symbol A in formula (II) represents end-groups. Preferred A group is a nucleophile. Each A is independently selected from the group consisting of H, $NH_2$, hydrocarbyl, hydroxyl, carboxyl, thio, amidyl, alkylthio, aryloxy, alkylamino, arylamino, heterocyclyl, heteroaryl, dialkylamino and diarylamino. Preferred end-groups include, but are not limited to, alkylamino, dialkylamino, diarylamino, morpholinyl, optionally substituted piperazinyl, optionally substituted piperidinyl, optionally substituted azetidinyl and optionally substituted pyrrolidinyl. More preferred end-groups include morpholinyl, N-methyl piperazinyl, N-ethyl piperazinyl, dimethylamino, diethylamino, and 1-methyl-4-methylamino-piperidinyl, benzyl-1-piperazinyl carboxylate.

Symbols $B^1$, $B^2$ and $B^3$ in formulas (II) represent another type of end-groups. Preferred $B^1$, $B^2$ and $B^3$ are independently an electrophile. Each of $B^1$ and $B^2$ can be independently H, hydroxyl or hydrocarbyl. Suitable agents that can form end-groups $B^1$, $B^2$ and $B^3$ include, but are not limited to, acrylates, acrylamides, acrylic acids, alkanoyl halides, alkenyl halides, aryl halide, heteroaryl halide, arylalkyl halides, aldehyde, keones, tosyl halides, mesyl halides, alkyl halides, heteroalkyl halide, carboxylic acids, carboxylic acid anhydrides and isocyanates.

In some preferred embodiments, present invention provides compounds having the formula (IIa):

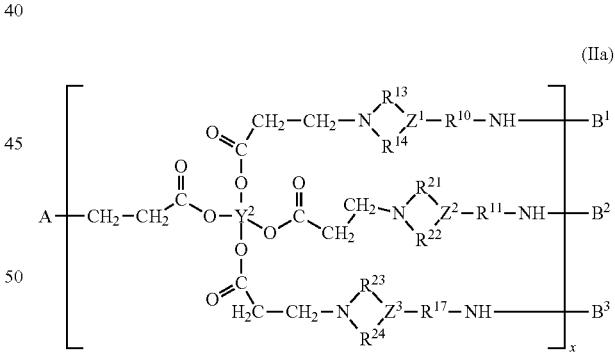

In formula (IIa), x is an integer from 1 to about 2000. Each of $R^{10}$, $R^{11}$, $R^{13}$, $R^{14}$, $R^{17}$, $R^{21}$, $R^{22}$, $R^{23}$ and $R^{24}$ is independently oxo, —S—, optionally substituted $C_{1-30}$ alkylene, optionally substituted $C_{2-30}$ alkenylene, optionally substituted $C_{2-30}$ alkynylene, optionally substituted $C_{3-8}$ cycloalkylene or optionally substituted $C_{6-18}$ arylene, any of which may optionally contain one or more heteroatoms selected from the group consisting of N, O and S. Preferably, each of $R^{10}$, $R^{11}$, $R^{13}$, $R^{14}$, $R^{17}$, $R^{21}$, $R^{22}$, $R^{23}$ and $R^{24}$ is independently $C_{1-30}$alkylene, more preferably $C_{1-8}$alkylene, for example, $CH_2CH_2$. $Y^2$ is C, Si, tetralkyl, tetraarylene, tetraheteroalkylene, tetracycloalkylene or tetraheteroarylene. Preferred tetraalkyl includes $R^h(R^i—)_4$, wherein $R^h$ is C, Si or $C_{4-8}$tetracycloalkyl. $R^i$ can be H, $C_{1-30}$alkylene or $C_{1-30}$arylalkylene. Preferred tetraaryl includes $R^h(Ar^1—)_4$, wherein $Ar^1$ is arylene, heteroarylene. Preferably, $Ar^1$ is $C_{6-10}$arylene, $C_{8-12}$arylalkylene or $C_{4-6}$heteroarylene. The metal used can be Ti, Zr, Mn, Ge, Sn and the like. In some other preferred embodiments, $Y^2$ is C, Si, $(C_{1-30}$alkylene$)_4$C, $C_{8-12}$arylalkylene or $(C_{1-30}$alkylene$)_4$Si. In some more preferred embodiments, $Y^2$ is $(C_{1-8}$alkylene$)_4$C or $(C_{1-8}$alkylene$)_4$Si. In particular preferred embodiments, $Y^2$ is $(CH_2)_4$C, $(CH_2C_6H_4CH_2)_4$C or $(CH_2)_4$Si. $Z^1$, $Z^2$ and $Z^3$ are each independently N, CH, C—$(C_{1-8}$alkyl), C—$(C_{1-8}$heteroalkyl), C—$(C_{6-10}$aryl), C—$(C_{4-6}$heteroaryl), SiH, Si—$(C_{1-8}$alkyl), Si—$(C_{1-8}$heteroalkyl), Si—$(C_{6-10}$aryl), Si—$(C_{4-6}$heteroaryl) or a metal, such as Ti or Zr. End-group A is defined the same as above for formulas (I), (Ia) and (II). End-groups $B^1$, $B^2$ and $B^3$ are defined the same as above for formulas (I), (Ia) and (II)

In a different aspect, the present invention provides a compound having the formula:

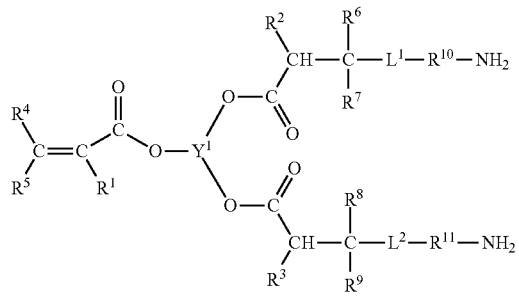

(III)

In the above formula (III), all the substituents are the same as defined above for formula (I). Each of $R^1$, $R^2$ and $R^3$ can be independently H or hydrocarbyl, preferably, hydrogen, deuterium or alkyl. Each of $R^4$, $R^5$, $R^6$, $R^7$, $R^8$ and $R^9$ is H or hydrocarbyl. The hydrocarbyl is preferably alkyl or heteroalkyl, and do not have a primary, a secondary or a carbon-carbon double bond conjugated to a carbonyl group. Each of $L^1$ and $L^2$ is independently selected from the group consisting of $NR^{12}$ and $N(—R^{13}—)(—R^{14}—)Z$, wherein each $R^{12}$ is independently hydrocarbyl, hydroxyl or thiohydroxyl and each of $R^{13}$ and $R^{14}$ is bonded to N and Z to form a cyclic structure. In some preferred embodiments, $L^1$ and $L^2$ are $N(—R^{13}—)(—R^{14}—)Z$. Each of $R^{10}$, $R^{11}$, $R^{13}$ and $R^{14}$ is preferably independently optionally substituted $C_{1-30}$ alkylene, more preferably $C_{1-8}$alkylene Z is preferably N, CH, $CC_{1-8}$alkyl, SiH, $SiC_{1-8}$alkyl or a metal selected from the group consisting of B, Al, Ga and In. Preferred $Y^1$ includes C-alkyl, CH, $(C_{1-8}$alkylene$)_3$, and $(C_{1-8}$alkylene$)_3$N. In another preferred embodiment, $R^1$, $R^2$ and $R^3$ are H or $CH_3$; $R^4$, $R^5$, $R^6$, $R^7$, $R^8$ and $R^9$ are H or deuterium; $L^1$ and $L^2$ are $N(CH_2CH_2)Z$, where Z is N, CH or $C_{1-8}$alkyl; $R^{10}$ and $R^{11}$ are $CH_2CH_2$.

In still a different aspect, the present invention provides a compound having the formula:

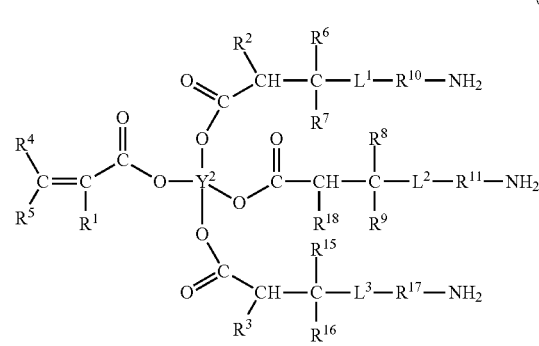

(IV)

The substituents are the same as defined for formula (II).

In certain aspects, the compounds can be copolymers or blends of poly(amino ester)s of formula (I) and formula (II). In one embodiment, the compound can be a block copolymer of poly(amino ester)s having formula (I) and formula (II). In another embodiment, the compound can be a random copolymer of poly(amino ester)s having formula (I) and formula (II). In yet another embodiment, the compound can be an alternating copolymer of poly(amino ester)s having formulae (I) and (II). In still another embodiment, the compound can be a blend of poly(amino ester)s having formulae (I) and (II). In still other embodiment, the compound can be a copolymer of poly(amino ester)s having formula (I) and/or (II) and a linear unit.

METHODS OF PREPARING POLY(AMINO ESTER) COMPOUNDS

In one aspect, the present invention provides a method for preparing a branched, or dendritic, or hyperbranched poly (amino ester) compound. The method includes reacting an acrylate monomer having the formula:

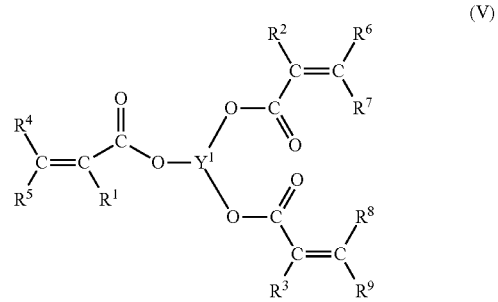

(V)

with a diamine monomer having a formula selected from the group consisting of:

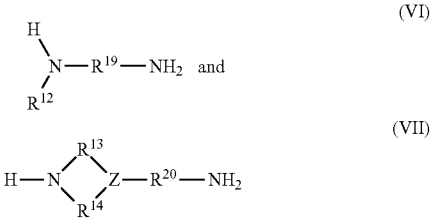

(VI)

(VII)

$R^1$, $R^2$ and $R^3$ are the same as defined for formulae (I)-(III). $R^4$, $R^5$, $R^6$, $R^7$, $R^8$, $R^9$ and $R^{12}$ are defined the same as for formulas (I) and (II). $R^{13}$ and $R^{14}$ are defined the same as for formulae (I)-(III). Z is defined the same as for formulae (I)-(III).

Each of $R^{19}$ and $R^{20}$ can be independently oxo, —S—, optionally substituted $C_{1-30}$ alkylene, optionally substituted $C_{2-30}$ alkenylene, optionally substituted $C_{2-30}$ alkynylene, optionally substituted $C_{3-8}$ cycloalkylene or optionally substituted $C_{6-18}$ arylene, any of which may optionally contain one or more heteroatoms selected from the group consisting of N, O and S. In some preferred embodiments, $R^{19}$ and $R^{20}$ can be optionally substituted $C_{1-30}$ alkylene, optionally substituted $C_{3-8}$ cycloalkylene or optionally substituted $C_{6-10}$ arylene. More preferably, $R^{19}$ and $R^{20}$ are optionally substituted $C_{1-30}$ alkylene, for example, $C_{1-8}$alkylene, such as $(CH_2)_n$, wherein n is an integer from 1 to 8.

In another aspect, the present invention provides a method for preparing a branched poly(amino ester). The method includes homopolymerizing a monoacrylate monomer having the formula (III) or formula (IV).

method for preparing a branched poly(amino ester). The method includes reacting an acrylate monomer having the formula:

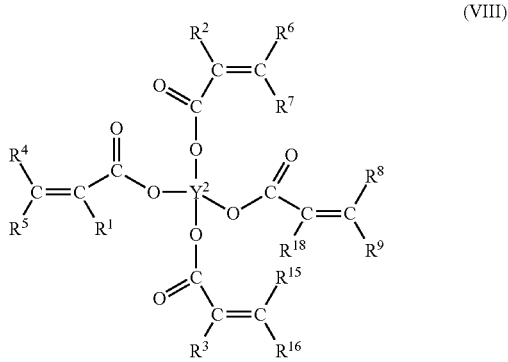

(VIII)

with a diamine monomer having formula (VI) or (VII).

The substituents in formula (VIII) are defined the same as for formula (I). For instance, $R^1$, $R^2$ and $R^3$ are defined the same as for formula (II). $R^4$, $R^5$, $R^6$, $R^7$, $R^8$, $R^9$, $R^{15}$ and $R^{16}$ are defined the same as for the corresponding substituents in formula (II). $Y^2$ is defined the same as for the corresponding substituents in formula (II).

In certain instances, poly(amino ester)s having more secondary amino groups may be preferred because secondary amines are more readily protonated than are tertiary amines and may improve the utility of the poly(amino ester), for example by enhancing water-solubility or enhancing the ability of the poly(amino ester) to interact with a bioactive agent. Secondary amino groups can be introduced into the polymer via addition of linear poly(amino ester)s having secondary amine linkages in the polymer backbones or units of formula (VI) or formula (VII).

In some embodiments, the poly(amino ester)s of the present invention can have between 1 to 2000 linear units. For example, the poly(amino ester)s can contain at least 0.1%, at least 1%, at least 20%, at least 30%, at least 35%, at least 40%, at least 45%, at least 50%, at least 55%, at least 60%, at least 65%, at least 70%, at least 75%, at least 80%, at least 85%, at least 90%, at least 95%, at least 97%, at least 98%, or at least 99% linear units of.

In certain other embodiments, the poly(amino ester)s of the present invention can have between 1 to 2000 dendritic units of formula (I), formula (II), formula (VI) or formula (VII). For example, the poly(amino ester)s can contain at least 0.1%, at least 1%, at least 20%, at least 30%, at least 35%, at least 40%, at least 45%, at least 50%, at least 55%, at least 60%, at least 65%, at least 70%, at least 75%, at least 80%, at least 85%, at least 90%, at least 95%, at least 97%, at least 98%, or at least 99% dendritic units of formula (I) or formula (II). In some embodiments, the dendritic units are optionally connected by at least one linear units.

The poly(amino ester)s of the present invention can contain between 1 to 2000 diamine units of formula (VI) or formula (VII). For example, the inventive poly(amino ester) can at least 0.1%, at least 1%, at least 20%, at least 30%, at least 35%, at least 40%, at least 45%, at least 50%, at least 55%, at least 60%, at least 65%, at least 70%, at least 75%, at least 80%, at least 85%, at least 90%, at least 95%, at least 97%, at least 98%, or at least 99% units of formula (VI) or formula (VII).

In some embodiments, the poly(amino ester)s can have asymmetric nitrogen in the polymer backbones. For example, in formula (I) and (III), $L^1$ and/or $L^2$ can contain asymmetric nitrogen groups when $R^{12}$ differs from the other substituents on the nitrogen or when $R^{13}$, $R^{14}$ and the third substituent are different from each other. Similarly, in formulae (II) and (IV), each of $L^1$, $L^2$ and $L^3$ can independently contain asymmetric nitrogen groups when $R^{12}$ differs from the other substituents on the nitrogen or when $R^{13}$, $R^{14}$ and the third substituent are different from each other. The diamine monomers used to prepare the poly(amino ester)s can also be asymmetrically substituted having a secondary amino group and a primary amino group that generally differ in reactivity. For example, in formula (VI), the monomer can have an asymmetric nitrogen when $R^{12}$, $R^{19}$ and H are different from each other. Similarly, in formula (VII), the monomer can have an asymmetric nitrogen when $R^{13}$, $R^{14}$ and H are different from each other. Z can also be an asymmetric nitrogen when $R^{13}$, $R^{14}$ and $R^{20}$ are different from each other or an asymmetric carbon when H, $R^{13}$, $R^{14}$ and $R^{20}$ are different from each other. In formula (V), the tris(acrylate) ester monomer can also be asymmetrical depending on the choice of substituents $R^1$, $R^2$, $R^3$, $R^4$, $R^5$, $R^6$, $R^7$, $R^8$ and $R^9$. In formula (VIII), the tetra(acrylate) ester monomer can also be asymmetrical depending on the choice of substituents $R^1$, $R^2$, $R^3$, $R^4$, $R^5$, $R^6$, $R^7$, $R^8$, $R^9$, $R^{15}$, $R^{16}$ and $R^{18}$. The reaction of an asymmetric diamine with a tris(acrylate)ester monomer can give rise to a number of diastereomeric dendrite units. The orientation of the substituents can be controlled by adjusting the reaction conditions.

In some embodiments, the branched poly(amino ester)s are atactic. In other embodiments, the branched poly(amino ester)s are isotactic or syndiotactic. In still other embodiments, the branched poly (amino ester)s have a plurality of asymmetric centers in the polymer backbones. In some further embodiments, the branched poly(amino ester)s are optically active.

The present invention also provides poly(amino ester)s having up to 10000 terminal or dendritic units. Preferably, the polymers can have terminal or dendritic units ranging from about 1 to 100, 50 to 200, 150 to 300, 200 to 500, 300 to 800, 700 to 1200, 1000 to 1600, 1500 to 2000, 1 to 2000, 2 to 2500 and 1 to 3000. In some embodiments, the molecular weight of the poly(amino ester)s can range from about 400 g/mol to approximately 600,000 g/mol, and preferably ranges from between approximately 400 g/mol and 100,000 g/mol.

FIG. 1 illustrates one aspect of the present invention and the mechanism of the polymerization of a tris(acrylate) ester and a diamine. In one embodiment, the reaction is carried out by reacting trimethylpropane triacrylate (TMPTA) with a diamine having a secondary and a primary amino group, such as 1-(2-aminoethyl)piperazine (AEPZ). An (acrylate)$_1$(diamine)$_2$-type intermediate having one double bond functional groups and two amino groups is formed by reacting one equiv of tris(acrylate) with two equiv of diamines. For example, an intermediate TMPTA1-AEPZ2 is formed during the reaction. In one embodiment, further polymerization of the intermediate produces hyperbranched poly(amino ester)s having secondary and tertiary amines in the interior and primary amines in the peripheral. As exemplified in FIG. 1, the terminal units have an unreacted original primary amino group, which can further react with an end-capping agent, such as an acrylate, an acrylamide, an acrylic acid, alkanoyl chloride, an alkyl halide, an anhydride, an ester or an isocyanate; or with another bactch of linear or dendritic forming monmers, such as diacrylate/diamines, carbon tetraacrylate/diamines or pentaerythritol tetraacrylate to form copolymers.

In one embodiment, FIG. 1 shows that the linear or dendritic units can be linked to the polymer backbone through a linker having a tertiary amine and a secondary amine, wherein secondary amines having reduced activity can still react with acrylates.

Various commercially available acrylate monomers and diamine monomers can be used for the preparation of poly (amino ester)s. Suitable acrylate monomers include, but are not limited to, trimethylolpropane triacrylate, trimethylolpropane trimethacrylate, glycerol propoxylate (1PO/OH) triacrylate, pentaerythritol propoxylate triacrylate, pentaerythritol triacrylate, trimethylolpropane ethoxylate triacrylate ($M_n$=428, 604 or 912), trimethylolpropane propoxylate triacrylate ($M_n$=470 or 644), tris(2-(acryloyloxy)ethyl)isocyanurate, carbon tetraacrylate and pentaerythritol tetraacrylate.

Non-commercial acrylate monomers can be readily prepared using substitution reactions. In some embodiments, various triacrylate or tetraacrylate monomers can be prepared by reacting an acrylate with a molecue having a moiety bearing three or four leaving groups, respectively. Suitable leaving groups include, but are not limited to, a halide, a carboxylate, an alkoxy, an alcohol, a sulfonium, an ammonium, a sulfonyl and a sulfonate. For example, a triacrylate having a carbon-based center structure can be synthesized by reacting a carboxylate of an acrylate with an orthoester. A triacrylate having a silicon containing center structure can be synthesized by reacting a carboxylate of an acrylate with an alkylsiloxane or trihaloalkylsilane. A tetraacrylate monomer having a cabon-based center can be synthesized by reacting an acrylate, such as a carboxylate of an acrylate with a molecule having four leaving groups. A tetraacrylate monomer can be formed by reacting a caroxylate of an acrylate with a silyl group bearing leaving groups, such as a siloxane or a tetrahalosilane.

The present invention also contemplates the preparation and isolation of key intermediates, such as compounds having formulae (III) and (IV). The present invention also provides the methods of homopolymerization of compounds having the formula (III) or (IV) to form hyperbranched polymers. The methods offer the advantage of precisely controlled feed ratios and number of branches or the degree of branching in the polymer backbones. In some embodiments, the monomers having formula (III) can be prepared by reacting a triacrylate with two equiv of diamines. The monomers having formula (IV) can be prepared by reacting a tetraacrylate with three equiv of diamines. In some embodiments, the polymerizations are carried out by self-initiated polymerization of monomers having formula (III) or (IV). In other embodiments, the polymerizations can be initiated in the presence of an agent, such as a catalyst. Suitable agents can be a base, such as an amine; or an acid, such as $H^+$ or a metal ion: In some further embodiments, hyperbranched copolymers can be prepared by polymerizing a mixture of monomers having formulae (III) and (IV). Hyperbranched block copolymers can be prepared by sequential polymerization of monomers having formulae (III) and (IV).

Suitable diamine monomers that can be used to prepare poly(amino ester)s include, but are not limited to, 1-(2-aminoethyl)piperazine, N-methyl ethylenediamine, 4-(aminomethyl)piperidine, 4-amino-piperidine, 3-aminopyrrolidine, N-ethylethylenediamine, N-methyl-1,3-propanediamine, N-isopropylethylenediamine, N-hexylethylenediamine, N-butylethylenediamine, N-(2-hydroxypropyl)ethylenediamine, and N,N-diethyldi-ethylene triamine.

Various feed molar ratios of diamine and acrylate can be used. In some embodiments, the molar ratio of diamine monomer to tris(acrylate ester)monomer can range from about 4:1 to about 1:4; about 2:1 to about 1:2; and about 2:1 to about 1:1. Preferred feed molar ratios are those that can avoid gelation during the polymerization. In other embodiments, the molar ratio of diamine monomer to tetra(acrylate ester)monomer can range from about 6:1 to about 1:6; about 3:1 to about 1:3; and about 3:1 to about 1:1. Preferred feed molar ratios are those that can avoid gelation during the polymerization.

The reaction can be carried out over a wide range of temperatures and pressures. For example, the reaction can be carried out between about −20° C. and about 100° C. Preferably, the reaction is incubated between about −10° C. and about 90° C., more preferably between about 0° C. and about 80° C., even more preferably, between about 10° C. and about 70° C., still more preferably between 20° C. and 50° C. In some embodiments, the reaction can be incubated for a period from about 10 hours to about 40 days, such as 10 hrs to 24 hrs, 1 to 3 days, 3 to 7 days, 5 to 10 days, 8 to 15 days, 12 to 20 days, 18 to 30 days, 25 to 35 days, 30 to 40 days. For example, when the ratio of tris(acrylate)ester to diamine used is about 1:2, the reaction is preferably incubated for between 24 hours and 240 hours, more preferably between 24 and 168 hours. In another example, when the ratio of tetra(acrylate)ester to diamine used is about 1:3, the reaction is preferably incubated for between 10 hours and 300 hours, more preferably between 24 and 200 hours. Pressure can also be optionally applied to the reaction system.

The reaction can be carried out either in neat or in the presence of a solvent. Preferably, the reaction is carried out in the presence of a solvent. Solvents that can be used include, but are not limited to, water, organic solvents and combinations thereof. The organic solvents used include, but are not limited to, $C_{1-8}$alcohols, such as methanol, ethanol, isopropanol, butanol, pentanol, hexanol, heptanol and octanol; a ketone, such as acetone; a chlorinated solvent, such as chloroform, dichloromethane, methyl chloride, carbon tetrachloride, dichloroethane, tetrachloroethane; a chroinated aromatic solvent; tetrahydrofuran; $C_{3-8}$alkanes, such as propane, butanes, pentanes, hexanes, heptanes and octanes; an aromatic solvent, such as toluene, benzene, xylenes; glywe; an ether, such as diethyl ether; dimethylsulfoxide; an amide, such as dimethylformamide and dimethylacetamide; and combinations thereof.

The monomers and the poly(amino ester)s prepared can be used directly or prepurified prior to use. Purification can be achieved by techniques known in the art, including, but not limiting to, precipitation, crystallization, chromatography, drying under vacuum, and the like. For example, the poly (amino ester) can be purified by precipitation with a solvent, such as acetone containing an acid, such as hydrochloric acid (HCl), and subsequently washed with acetone and then dried under vacuum. The poly(amino ester)s of present invention can also be purified by precipitation with ether, and then washed with fresh ether and dried under vacuum. The monomers prepared can be purified by flash chromatography and/or recrystallization.

In some embodiments, the secondary amino groups or terminal primary amino groups formed in the poly(amino ester)s, are further reacted with an end-capping agent. End-capping agent can be an electrophile. Suitable end-capping reagents include, but are limited to, acrylates, acrylamides, an acrylic acid, an alkanoyl halide, an aroyl halide, an alkenoyl halide, an alkyl halide, an tosyl halide, an mesyl halide, an ester, an anhydride, a thionyl chloride and an isocyanate.

In one aspect, the degree of branching in the poly(amino ester) can be controlled by varying the type of monomers used and the relevant amounts thereof present in the reaction. For instance, the use of an excess of tris(acrylate ester)monomer can increase the degree of branching. In some embodiments, the molar ratio of tris(acrylate ester) and diamine can change from about 1:1.5 to 1:3, and preferably about 1:2. The molar ratio of tetracrylate and diamine can change from about 3:1 to 1:4, 2:1 to 1:4, 1:1 to 1:4, 1:1.3 to 1:4, 1:1.5 to 1:4, 1:1.5 to 1:4, 1:2 to 1:4, 1:3 to 1:4 and preferably about 1:3. Although increasing the amount of tris(acrylate ester)monomer relative to diamine monomer can increase the degree of branching in the poly(amino ester), longer reaction times may be required to complete the reaction. In another aspect, the degree of branching can also be varied by adjusting the reaction temperature, time and solvents.

The structure of the compounds obtained by the foregoing reactions can be characterized by a number of analytical methods, such as $^{13}$C NMR spectroscopy. For instances, $^{13}$C NMR spectroscopy can be used to identify and/or to confirm the presence or absence of carbon atoms that are linked to a primary amino group, a secondary amino group or a tertiary amino group in the polymer backbone.

FIG. 2 illustrates an embodiment of the present invention. For example, in FIG. 2, eight peaks are observed in the $^{13}$C NMR spectrum of the poly(amino ester) prepared from the polymerization of trimethylpropane triacrylate (TMPTA) and 1-(2-aminoethyl)piperazine (AEPZ), with a feed monomer molar ratio of 1:2. The results show that the poly(amino ester) contains dendritic units having secondary and tertiary amine linkages as well as terminal units having primary and tertiary amine linkages. For example, peak ($a_1$) located at 42.6 ppm corresponds to carbons linked to the primary amines; peaks ($a_2$ and $g_2$) located at 43.5 ppm and 41.2 ppm correspond to carbons linked to the secondary amines; peaks ($b_1$, $b_2$, $C_1$, $C_2$, $d_1$, $d_2$, $e_1$ and $e_2$) located at 51.4 ppm, 52.5 ppm, 48.8 ppm, 48.8 ppm, 48.4 ppm, 48.4 ppm, 51.9 ppm and 51.9 ppm correspond to carbons linked to the tertiary amines. The ratio of the absorption intensity of the two peaks at 42.6 ppm and 43.5 ppm determined using an inverse-gated broadband decoupled technique (INVGATE) is close to 1:1. FIG. 1 illustrates that poly(amino ester)s having high molecular weight can be prepared by the polymerization of (acrylate)(diamine)$_2$- type intermediate generated in-situ. In some embodiments, the preent invention also contemplates the polymerization of isolated (acrylate)(diamine)$_2$-type intermediate as monomer to obtain high molecular weight poly(amino ester)s.

BIOACTIVE COMPOSITIONS

The branched poly(amino ester) compounds of the present invention have the advantage of superior solubility, good biodegradability and biocompatibility. Because of the uniques hyperbranched structure and high density of amine groups, the compounds are highly soluble in either aqueous or organic solvents and can be readily degraded in aqueous solution. The good biodegradability property of the compounds may be in part attributed to the facile hydrolysis of the ester linkages under physiological conditions. To use as a vector in delivering bioactive agents to cells and tissues either in vivo or in vitro, it is essential for the compound to be biocompatible and biodegradable. The present invention contemplates that the branched, dendritic or hyperbranched poly(amino ester)s can be made both biocompatible and biodegradable using non-toxic monomers. In one aspect, non-toxic monomers, such as acrylates are used as starting materials for the preparation of poly(amino ester)s.

Various bioactive agents can be delivered by the compounds of the present invention either in vivo or in vitro. The agents can be therapeutic, diagnostic or prophylactic agents. The agents can be, for example, a small molecule, organometallic compounds, nucleic acid, protein, peptide, polynucleotide metal, an isotopically labelled chemical compound, a drug, a vaccine, an immunological agent, and the like. The agent can be described as a single entity, a compound or a combination of entities or compounds.

In one embodiment, the bioactive agent is a compound with pharmaceutical activity, such as a clinically useful drug. Suitable drugs include, but are not limited to: an antibiotic, an anti-viral agent, an anesthetic, an steroidal agent, an anti-inflammatory agent, an anti-neoplastic agent, an antigen, a vaccine, an antibody, a decongestant, an antihypertensive, a sedative, a birth control agent, a progestational agent, anticholinergic, an analgesic, an anti-deptessant, an anti-psychotic, a diuretic, a cardiovascular active agent, a vasoactive agent, a non-steroidal anti-inflammatory agent and a nutritional agent.

The bioactive agent to be delivered can also be an agent for use in diagnosis or screening. Diagnostic agents that can be delivered in vivo by the poly(amino ester)s of the present invention include gases, metals, commercially available imaging agents used in positron emission tomography (PET), computer assisted tomography (CAT), x-ray, fluoroscopy, magnetic resonance imaging (MRI) and contrast agents. Examples of suitable materials for use as contrast agents in MRI include gadolinium chelates, iron, magnesium, manganese, copper, chromium and their chelates. Examples of materials useful for CAT and x-ray imaging include iodine-based materials. In one embodiment, dendritic poly(amino ester)s are used as biocompitable imaging agents.

Prophylactic agents that can be delivered by the poly(amino ester)s of present invention include, but are not limited to, antibiotics, nutritional supplements, and vaccines. Vaccines can comprise isolated proteins or peptides, inactivated organisms and viruses, dead organisms and viruses, genetically altered organisms or viruses, and cell extracts.

In one embodiment, the bioactive agent to be delivered by the poly(amino ester)s of the present invention is a polynucleotide. A polynucleotide can be any nucleic acid, including, but not limiting to, RNA and DNA. The polynucleotide can be of any size and sequence, and they may be single- or double-stranded. The polynucleotide can, for example, be greater than 1000 base pairs long or even greater than 10,000 base pairs long. In some preferred embodiments, the polynucleotide is purified prior to use and is substantially free from contaminants, i.e. the polynucleotide is preferably more than about 50% pure, more preferably more than about 75% pure, and even more preferably greater than about 95% pure. The polynucleotide can be obtained by any means known in the art. Specifically, the polynucleotide can be engineered using recombinant techniques. In addition, the polynucleotide can be obtained from natural sources and purified from contaminating components found normally in nature, or the polynucleotide may be chemically synthesized in a laboratory. For example, the polynucleotide is synthesized using standard solid phase chemistry. The polynucleotide can be modified by chemical or biological means, for example to increase stability of the polynucleotide. Methods for modification of polynucleotides include methylation, phosphorylation, end-capping, and the like. Derivatives of polynucleotides can also be used in the present invention. These derivatives include modification in the bases, sugars, and/or the phosphate linkage of the polynucleotide.

In order to deliver a bioactive agent, a poly(amino ester) of the present invention is contacted with the particular agent that is to be delivered to form a complex. When the bioactive agent carries a negative charge, it may be desirable to protonate the nitrogen atoms in the poly(amino ester)s (i.e. in the backbone of the poly(amino ester)s) prior to contacting the poly(amino ester)s with the bioactive agent, thereby providing a positively charged poly(amino ester)s that can associate with negative charges present in the bioactive agent to form a complex by electrostatic attraction. Alternatively, the monomers used to form the repeating unit can be selected to provide a poly(amino ester)s with functional groups that are available to form covalent bonds with a bioactive agent. In one embodiment, the poly(amino ester)s can form a complex by physically encapsulating the bioactive agent. In another embodiment, the poly(amino ester)s can form a complex through hydrogen bonding interactions.

The poly(amino ester)s-agent complex can be modified to include targeting agents to target a particular cell, collection of cells, nuclei, or tissues or to promote endocytosis or phagocytosis of the complex. The targeting agents may be attached to the poly(amino ester)s of the present invention through covalent links, and in some cases can be added during the formation of the poly(amino ester)-agent complex. In one embodiment, the targeting agents may stay on the surface of the complex system. Examples of targeting agents include, but are not limited to, proteins, peptides, carbohydrates, glycoproteins, lipids, small molecules, antibodies, fragments of antibodies, low-density lipoproteins (LDLs), transferrins, asiaglycoproteins, HIV gp120 envelope protein, receptor ligands, sialic acid and the like.

In one embodiment, a poly(amino ester)s-agent complex is formed through the contacting of a polynucleotide or salt thereof with a poly(amino ester) of present invention. For this purpose, the poly(amino ester)s are preferably at least partially protonated so as to electrostatically interact with the negatively charged polynucleotide. The poly(amino ester)s can be protonated, for example, by solubilizing the poly (amino ester)s in an aqueous solution of a pH suitable to protonate at least the primary amines present in the poly (amino, ester)s. The poly(amino ester)s-polynucleotide complex may form nano-particles that can then be used to deliver the polynucleotides to cells. The poly(amino ester)s-polynucleotide complex system can be used to protect the polynucleotide so as to at least partially prevent degradation during the delivery and up-take process. By neutralizing the charge on the backbone of the polynucleotide, the neutral or slightly-positively-charged poly(amino ester)s-polynucleotide complex may pass more easily through the hydrophobic membranes of the cell.

In another aspect, the poly(amino ester)s-polynucleotide complex described above can be used to deliver therapeutic genes to cells of an individual in vitro or in vivo. General methods for gene therapy are known in the art. See, for example, U.S. Pat. No. 5,399,346 incorporated herein by reference. A biocompatible capsule for delivering genetic material is described in PCT Publication WO 95/05452 incorporated herein by reference. Methods of gene transfer into hematopoietic cells have also previously been reported (see Clapp, D. W., and et al., Blood 1991, 78, 1132-1139; Anderson, Science 2000, 288, 627-629; and Cavazzana-Calvo and et al., Science 2000, 288, 669-672). It is known that naked DNA may be introduced into cells by complexing the DNA to a cation, such as polylysine, which is coupled to a ligand for a cell-surface receptor (see for example Wu, G. and et al *J. Biol. Chem.* 1988, 263, 14621; Wilson and et al. J. Biol. Chem. 1992, 267, 963-967; and U.S. Pat. No. 5,166,320). Binding of the DNA-ligand complex to the receptor may facilitate uptake of the DNA by receptor-mediated endocytosis. A DNA-ligand complex linked to adenovirus capsids which disrupt endosomes, thereby releasing material into the cytoplasm, may be used to avoid degradation of the complex by intracellular lysosomes (see for example Curiel and et al. Proc. Natl. Acad. Sci. USA 1991, 88, 8850; Cristiano and et al. Proc. Natl. Acad. Sci. USA 1993, 90, 2122-2126). Thus, the poly(amino ester)-nucleotide complex of the present invention may be used, either alone or in combination with a targeting agent, in receptor-mediated polynucleotide uptake, viral-mediated transfection or non-viral transfection.

Compositions containing a poly(amino ester)s-polynucleotide complex of present invention may optionally contain other transfection-facilitating compounds. A number of such compositions are described in WO 93/18759, WO 93/19768, WO 94/25608, and WO 95/02397 incorporated herein by reference. They include spermine derivatives useful for facilitating the transport of DNA through the nuclear membrane (see, for example, WO 93/18759) and membrane-permeabilizing compounds such as GALA, Gramicidine S, and cationic bile salts (see, for example, WO 93/19768).

In various embodiments, the poly(amino ester)s-agent complex of present invention can be used therapeutically in pharmaceutical compositions or medicaments to prevent or treat various diseases. The present invention provides methods of medical treatment, in which a therapeutic dose of a poly(amino ester)s-therapeutic agent complex is administered in a pharmacologically acceptable formulation, e.g. to a patient or subject in need thereof. Accordingly, present invention also provides pharmaceutical compositions comprising a therapeutically active compound complexed with a poly (amino ester)s of present invention and a pharmacologically acceptable excipient or carrier. The pharmaceutical composition may be soluble in an aqueous solution at a physiologically acceptable pH.

Depending on the intended mode of administration, the pharmaceutical compositions may be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The composition can include, as noted above, an effective amount of the selected drug in combination with a pharmaceutically acceptable carrier and, in addition, may include other medicinal agents, pharmaceutical agents, carriers, adjuvants, diluents, the like The administration in vivo can be performed by parenteral administration, e.g., by intravenous injection including regional perfusion through a blood vessel supplying the tissue(s) or organ(s) having the target cell(s). Other means of administration can include inhalation of an aerosol, subcutaneous, intraperitoneal, or intramuscular injection, direct transfection into, e.g., bone marrow cells prepared for transplantation into an organ that is subsequently transplanted into the subject. Further administration methods can include oral administration, particularly when the complex is encapsulated, or rectal administration, particularly when the complex is in suppository form.

Pharmaceutical compositions typically must be sterile and stable under the conditions of manufacture and storage. The composition can be formulated as a solution, microemulsion, liposome, freeze-dried powder, spray-dried powder or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be prefetable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, a poly(amino ester)-agent complex can be administered in a time release formulation, for example in a composition which includes a slow release polymer. The active compounds can be prepared with carriers that will protect the compound against rapid release, such as a controlled release formulation, including implants and microencapsulated delivery systems. For this purpose, biodegradable, biocompatible polymers can be used, including, but not limited to: ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the poly(amino ester)s-agent complex in the required amount in an appropriate solvent with one, or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying, freeze-drying and spray-drying which yields a powder of the active ingredient plus any additional desired ingredient from a previously sterile-filtered solution thereof. In accordance with an alternative aspect of present invention, a poly(amino ester)-agent complex may be formulated with one or more additional compounds that enhance the solubility of the poly(amino ester)s agent complex.

In accordance with another aspect of present invention, pharmaceutical compositions of the present invention, comprising a poly(amino ester)s-agent complex, may be provided in containers or commercial packages which further comprise instructions for use of the poly(amino ester)s-agent complex for therapeutic use such as the prevention and/or treatment of various diseases.

The present invention also provides an imaging agent comprising a branched poly(amino ester)-targeting agent complex. In one embodiment, the branched poly(amino ester) compounds can be used as a label. The fluorescence wavelengths and intensity can be adjusted by changing the molecular weights, degree of branching and solvents used. The imaging agent can comprise hyperbranched poly(amino ester) homopolymers, copolymers or blends having various molecular weights and degrees of branching. The copolymers or blends can be copolymers or blends of hyperbranched poly(amino ester)s having different acrylate-diamine repeat units or copolymers or blends of hyperbranched poly(amino ester) with other linear or hyperbranched branched polymers. In one aspect, the targeting agent can be therapeutic targeting agent. In some embodiments, the targeting agent can be an antibody to the targeted protein expressed on cell surfaces including endothelial cell surface; alternatively, the targeting agent can be a binding partner of a targeted protein expressed on endothelial cell surface. In addition, the therapeutic targeting agent can also be an agent having an active agent component and a targeting agent component, in which the targeting agent component is: an agent that specifically binds to a targeted protein expressed on endothelial cell surface (e.g., an antibody to the targeted protein expressed on endothelial cell surface); or a specific binding partner of the targeted protein expressed on endothelial cell surface. In these embodiments, the active agent component can be, for example, a radionuclide; a chemotherapeutic agent; an immune stimulatory agent; an anti-neoplastic agent: an anti-inflammatory agent; a pro-inflammatory agent; a pro-apoptotic agent; a pro-coagulant; a toxin; an antibiotic; a hormone; an enzyme; a protein (e.g., a recombinant protein or a recombinant modified protein) a carrier protein (e.g., albumin, modified albumin); a lytic agent; a small molecule; aptamers; cells, including modified cells; vaccine-induced or other immune cells; nanoparticles (e.g., albumin-based nanoparticles); transferring; immunoglobulins; multivalent antibodies; lipids; lipoproteins; liposomes; an altered natural ligand; a gene or nucleic acid; RNA; siRNA; a viral or non-viral gene delivery vector; a prodrug; or a promolecule.

In another aspect, present invention also provides a method of using an imaging agent, which is comprised of branched poly(amino ester)-targeting agent complex. In one embodiment, a method of performing physical imaging of an individual, comprising administering to the individual an imaging agent comprising a targeting agent component and an branched poly(amino ester) component, wherein the targeting agent component specifically binds to a targeted protein expressed on the endothelial cell surface. Upon administration, the targeted imaging agents can be visualized noninvasively by conventional external detection means (designed for the imaging agent), to detect the preferential or specific accumulation in the neoplasm. In other embodiments, the present invention contemplates methods of delivering such imaging agents in vivo in a neoplasm-specific manner, and then assessing a biopsy sample for the presence of the imaging agent; the methods also pertain to delivering imaging agents in a neoplasm-specific manner to a tissue sample. In still other embodiments, the present invention provides methods of delivering such imaging agents in a neoplasm-specific manner to a tissue (e.g., tumor) sample. In some further embodiments, the present invention contemplates methods assessing an individual for the presence or absence of neoplasia, administering to the individual an agent of interest that comprises an imaging agent component and a targeting agent component, as described above, and assessing the individual for the presence or absence of a concentration of the agent of interest, wherein the presence of a concentration of the agent of interest is indicative of the presence of neoplasia.

Accordingly, the present invention further provides a commercial package comprising a poly(amino ester)s-agent complex or the above-mentioned compositions together with instructions for the prevention, diagnosis and/or treatment of a relevant disease.

The following examples are offered by way of illustration and not by way of limitation.

EXAMPLES

Materials and Reagents

Plasmid DNA (pCMV-Luc) (National Institute of Infectious Diseases, Tokyo, Japan). Plasmid DNA was amplified in *E. coli*, purified by Qiagen column according to the supplier's protocol (Qiagen, Hilden, Germany), re-suspended in TE (Tris 10 mM, EDTA 1 mM) buffer at a concentration of 1 mg/ml and stored in aliquots at −20° C.

1-(2-aminoethyl)piperazine (AEPZ), trimethylolpropane triacrylate (TMPTA), 3-(4,5-dimethylthiazol-2-yl)-2,5-diphenyl tetrazolium bromide (MTT) and pentaerythritol tetraacrylate were purchased from Aldrich (Milwaukee, Wis., USA) and used without further purification. All other materials, including solvents, were used as received, i.e. without further purification.

General Characterization $^1$H NMR (400 MHz) and $^{13}$C NMR (100 MHz) spectra were recorded on a Bruker DRX-400 spectrometer. Gel permeation chromatography (GPC) was carried out on a Waters 2690 apparatus with a column (Waters Ultrahydrogel 500 and 250) and a Waters 410 refractive index detector using 0.5 M acetic acid/0.5 M sodium acetate as an eluent at a flow rate of 1.0 ml/min. The molecular weights were calibrated against poly(ethylene oxide) standards.

Example 1

Mechanism of the Polymerization and Structure of the Polymers

The reactivity sequence of the three types of amines in AEPZ is 2° amines (original)>1° amines>>2° amines (formed) in the Michael addition polymerization with diacrylates. When AEPZ was used in the polymerization with triacrylates, the reactivity sequence of the three types of amines in AEPZ may be similar to that reported in the polymerization with diacrylates because tricarylates and diacrylates have similar vinyl chemistries. Therefore, in the polymerization of TMPTA and AEPZ with the molar ratio of 1:2, the reaction mechanism is expected as described in FIG. 1, i.e., first, two molar equiv of 2° amines (original) reacted with TMPTA to form an (acrylate)$_1$(amino)$_2$-type intermediate, then the hyperbranched polymer was obtained from the polymerization of the in situ generated (acrylate)$_1$(amino)$_2$-type intermediate. In situ monitoring of the polymerization of one equiv of TMPTA with 2 equiv of AEPZ performed in CDCl$_3$ using $^{13}$C-NMR verified the formation of the (acrylate)$_1$(amino)$_2$-type intermediate. At the beginning of the reaction as shown in FIG. 1A, the only appearance of the new peaks a$_1$, b$_1$, c$_1$, d$_1$, e$_1$, and f$_1$ at ca. 39.1 ppm, 61.4 ppm, 53.3 ppm, 53.2 ppm, 53.8 ppm and 32.6 ppm, and reduced intensity of peaks a$_0$, b$_0$, c$_0$ and d$_0$ at ca. 38.9 ppm, 62.1 ppm, 55.0 ppm and 46.4 ppm, respectively indicates that the most reactive 2° amines (original) reacted with TMPTA to form an (acrylate)$_1$(amino)$_2$-type intermediate. FIG. 1B shows that with the progress of the polymerization, all the AEPZ monomers were consumed as indicated by the total disappearance of its characteristic resonances, such as peak b$_0$ at 62.1 ppm, and some oligomers from the polymerization of (acrylate)$_1$(amino)$_2$-type intermediate were formed as demonstrated by the new peaks such as a$_2$, b$_2$, g$_2$ and h$_2$ at ca. 46.6 ppm, 58.1 ppm, 45.5 ppm and 35.1 ppm, respectively. Further, FIG. 1C shows that the hyperbranced poly(amino ester)s with high molecular weight were obtained as reflected by the total disappearance of the vinyl resonances and almost same intensity of the peaks a$_1$ and a$_2$ at ca. 39.1 ppm and 46.6 ppm. On the basis of the mechanism described in FIG. 1, hyperbranched poly(amino ester)s containing secondary and tertiary amines in the interior and primary and tertiary amines in the peripheral can be prepared.

Example 2

General Procedure for the Synthesis of Hyperbranched, poly(amino ester)s

An acrylate monomer having n optionally substituted carbon-carbon double bonds, where n is an integer from 3 to 6, and each of the double bonds is in conjugation with a carbonyl group of an acrylate functionality. The monomer is dissolved in a solvent and treated with (n-1) equiv of diamine monomer. The polymers formed are collected and dried in vacuum. The structure of the polymers is determined by various analytical methods.

Example 3

Synthesis of Hyperbranched poly(TMPTA1-AEPZ2)

AEPZ (10.8 mmol) was dissolved in chloroform (15 ml) at room temperature. TMPTA (5.4 mmol) was added dropwise to the solution while stirring, followed by rinsing with 5 ml of chloroform. The mixture was stirred at ambient temperature for about a week. The product was precipitated from the reaction using 400 ml of acetone containing 5 ml of hydrochloric acid (10 M). The precipitate was collected, washed with fresh acetone and dried in a vacuum at 50° C. for 5 days.

Example 4

Characterization of Hyperbranched poly(amino ester)s

A water-soluble poly(amino ester)s was obtained having an average molecular weight of 19100 g/mol with a broad molecular weight distribution index of 2.32 as determined by GPC.

$^{13}$C NMR spectroscopy was performed to verify the structure of the compound. As shown in FIG. 2, the product has one type of carbon linked to the primary amines with peak (a$_1$) located at 42.6 ppm, two types of carbons linked to the secondary amines with peaks (a$_2$ and g$_2$) located at 43.5 ppm and 40.3 ppm, respectively, and eight types of carbons linked to the tertiary amines, as reflected by only five peaks at 48.4 ppm (d$_1$+d$_2$), 48.8 ppm (C$_1$+C$_2$), 51.4 ppm (b$_1$), 51.9 ppm (e$_1$+e$_2$), 52.5 ppm (b$_2$) due to the similar chemical environment of carbons of c$_1$ with c$_2$, d$_1$ with d$_2$ and e$_1$ with e$_2$. These results indicate that the poly(amino ester) having secondary and tertiary amines in the interior and primary and tertiary amines in the peripheral (as shown in. FIG. 2) was successfully prepared.

Figure 3:
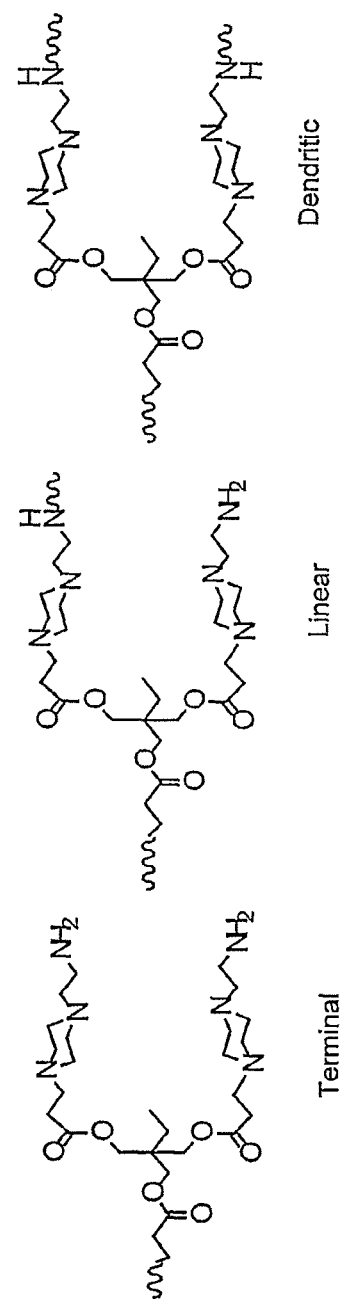
FIG. 3 illustrates the structures of the terminal, linear and dendritic units of hyperbranched poly(amino ester)s (poly (TMPTA1-AEPZ2)) formed when the (TMPTA)(AEPZ)$_2$ intermediate is used as a starting monomer to carry out the polymerization.

The degree of branching (DB) is one of the most important parameters for the structural characterization of hyperbranched polymers. The DB of poly(TMPTA1-AEPZ2) was assessed by taking the (acrylate)$_1$(amino)$_2$-type intermediate as a starting monomer, the terminal, linear and dendritic units are shown in FIG. 3. However, the structural difference among the terminal, linear and dendritic units as defined in FIG. 3 cannot be clearly distinguished using $^1$H or $^{13}$C NMR, so the DB according to this definition was difficult to be measured.

Example 5

Biodegradation Studies of Hyperbranched poly(amino ester)s

Figure 4:
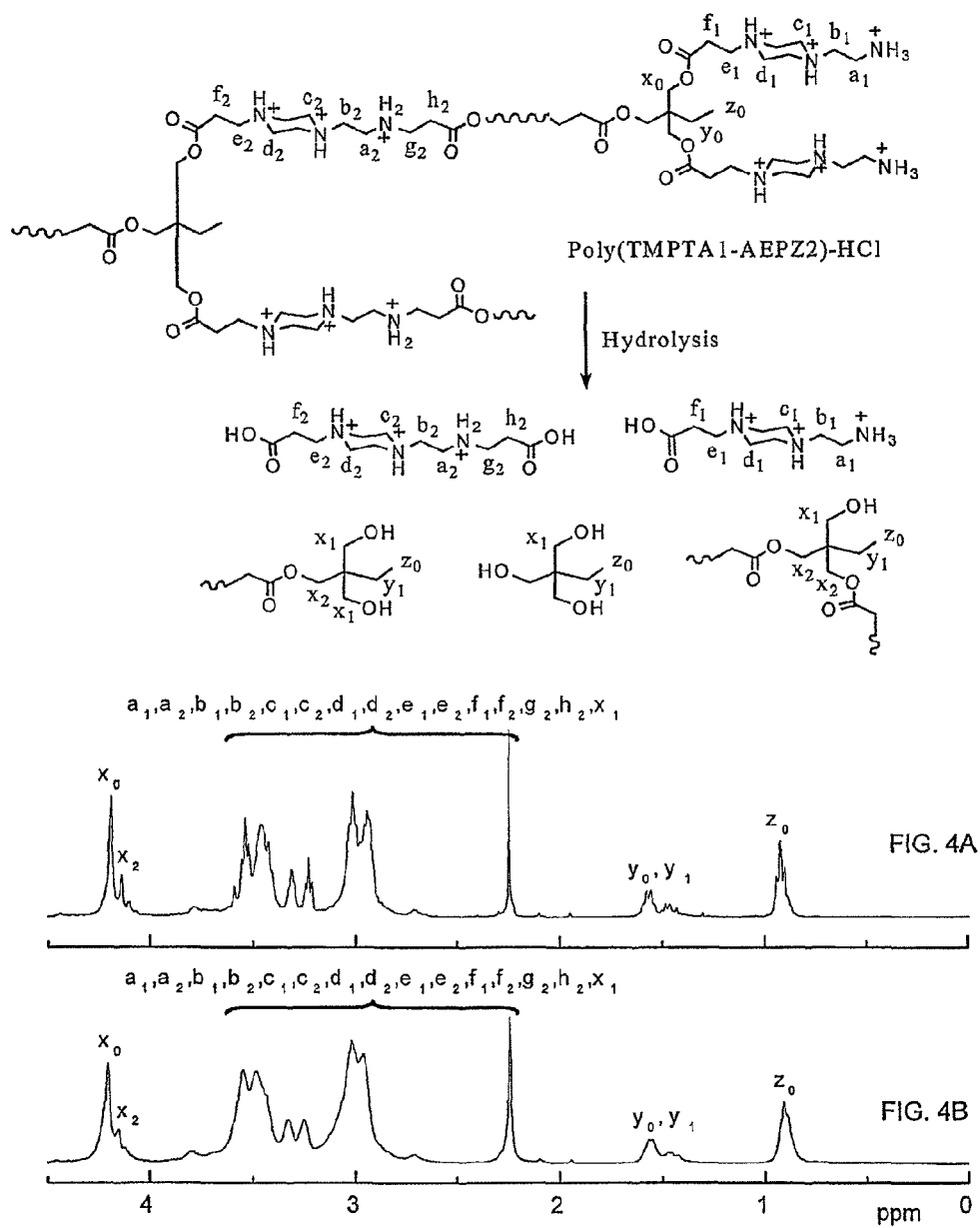
FIG. 4 shows the $^1$H-NMR spectra of protonated poly (amino ester)s, such as (poly(TMPTA1-AEPZ2)) after being incubated in water for a) 1 hour; and b) 11 days as shown in FIG. 4A and FIG. 4B, respecctively.

The poly(TMPTA1-AEPZ2) was tested for degradability. FIG. 4 depicts $^1$H NMR spectra of poly(TMPTA1-AEPZ2) in aqueous solution. Upon hydrolysis of the ester group, the peak attributed to the proton attached to the α carbon in the trimethylolpropane shifted from around 4.2 ppm to around 3.5 ppm. But the peak attributed to the proton attached to the methyl groups in the trimethylolpropane was unchanged at 0.9 ppm during the hydrolysis of the poly(TMPTA1-AEPZ2).

Therefore, the degree of hydrolysis can be monitored by the change in the ratio of the integrated intensities ($I_{4.2}/I_{0.9}$) of the two peaks at 4.2 ppm and 0.9 ppm. The results showed that ca. 12% of the ester bonds degraded in 11 days. Similar biodegradation is also observed for poly(PETA1-AEPZ3) compounds.

Example 6

Synthesis of and Characterization of Hyperbranched poly(PETA1-AEPZ3)

Hyperbranched poly(PETA1-AEPZ3)s are synthesized using a similar procedure as described in the above example 3. The reaction is carried out by dropwise addition of three equiv of diamine monomers to a pentaerythritol tetraacrylate (PETA) solution. The reaction is carried out at room temperature or an elevated temperature, such as between 40° C. to ° C. 80. The polymer formed can be precipitated in a solvent, such as acetone and dried in vacuum. The structure of the polymers are characterized by $^{13}$C NMR spectroscopy. Resonances similar to poly(TMPTA1-AEPZ2) are observed for the poly (PETA1-AEPZ3) compounds. The molecular weights are determined by GPC, which are in the range of 100000 g/mol to 1000000 g/mol.

Example 7

Synthesis and Isolation of TMPTA1-AEPZ2 Monomer

Monomer TMPTA1-AEPZ2 was synthesized by slow addition of AEPZ to a dilute solution of TMPTA in chloroform over a period of a week using a syringe pump. TMPTA1-AEPZ2 formed is isolated using a flash chromatography on silica gel or recrystilization. The compound is characterized by NMR and IR spectroscopy. The data from $^1$H, $^{13}$C NMR and mass spectroscopy confirm the formation of TMPTA1-AEPZ2 monmer.

Example 8

Synthesis of PETA1-AEPZ3 Monomer

PETA1-AEPZ3 is synthesized and isolated according to the similar procedure described for the preparation of TMPTA1-AEPZ2 in example 7. The structure of the compound is characterized by NMR and mass spectroscopy.

Example 9

Synthesis of Hyperbranched poly(TMPTA1-AEPZ2)s through the Polymerization of TMPTA1-AEPZ2

The polymerization of TMPTA1-AEPZ2 is carried out by dissolving the TMPTA1-AEPZ2 monomer in a solvent, such as chloroform and stir at room temperature for about a week. The polymer is isolated by precipitation into a solvent, such as acetone and dried in vacuum. The polymer is characterized by NMR spectroscopy and the molecular weights are determined using GPC.

Example 10

Polymerization of PETA1-AEPZ3

The polymerization is carried out similarly according to the procedure described in example 9. The polymers obtained are isolated by precipitation in acetone and dried in vacuum. The materials are further characterized by NMR and IR spectroscopy.

Example 11

Formation and Analysis of DNA/poly(amino ester)s Complexes

Plasmid DNA (pRE-Luc) was diluted to the selected concentration (usually 0.5-2.0 μg/μl) in 5% glucose, with vortexing. Various amounts of 0.1 M solution of poly(TMPTA1-AEPZ2) in 5% glucose was added slowly to the DNA solutions. The amount of poly(TMPTA1-AEPZ2) added was calculated based on chosen weight ratios of poly(TMPTA1-AEPZ2):DNA. After the solution was incubated at ambient temperature for 30 min with gentle vortexing, the poly (TMPTA1-AEPZ2)/DNA complexes were formed. The complexes were mixed with a loading buffer and loaded onto a 1% agarose gel containing ethidium bromide. Gel electrophoresis was run at room temperature in HEPES buffer (20 mM, pH=7.2) at 80 V for 60 min. DNA bands were visualized by an UV (254 nm) illuminator. Similarly, poly(PETA1-AEPZ3)/ DNA is formed by slow addition of 0.1 M solution of poly (PETA1-AEPZ3) in 5% glucose to a DNA solution.

Example 12

Effect of Weight Ratios on Retardation of DNA Migration

Figure 5:
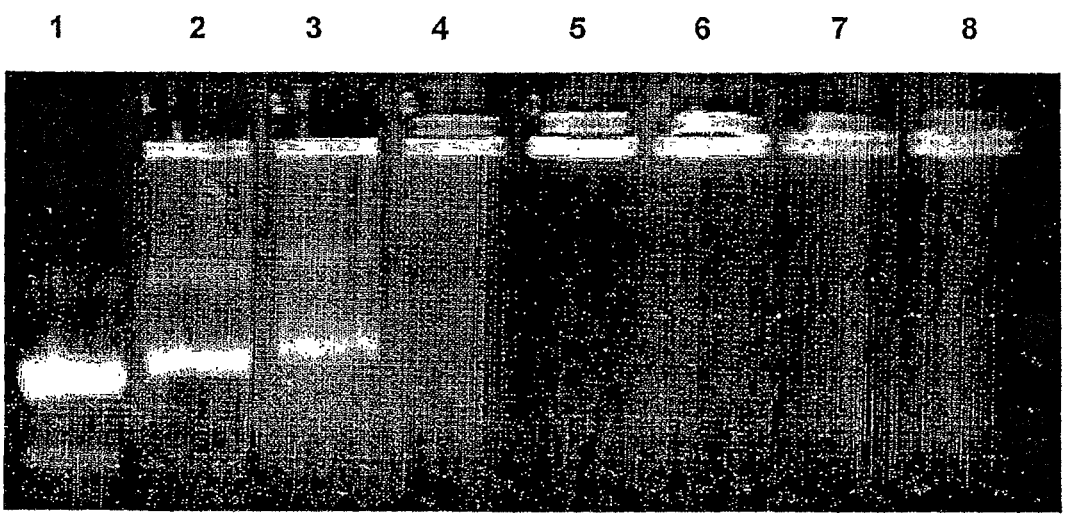
FIG. 5 illustrates the results of Agarose gel electrophoresis retardation of pRE-Luc DNA using hyperbranched poly (TMPTA1-AEPZ2). Each lane number corresponds to a different DNA/polymer weight ratio. For example, lane 1, ratio=1:0 (DNA only); lane 2, ratio=1:0.6; lane 3, ratio=1:0.8; lane 4, ratio=1:1; lane 5, ratio=1:1.5; lane 6, ratio=1:2; lane 7, ratio=1:3; and lane 8, ratio=1:4.

All the primary, secondary and tertiary amines in poly (TMPTA1-AEPZ2) were in the protonated form at physiological pH, enabling the poly(amino ester)s to interact with the negatively charged DNA. The results of the agarose gel electrophoresis in FIG. 5 demonstrate that the migration of DNA was retarded completely when the weight ratios of poly(TMPTA1-AEPZ2)/DNA were higher than 1.5:1. The complexes of poly(PETA1-AEPZ3) shows similar effect.

Example 13

Figure 6:
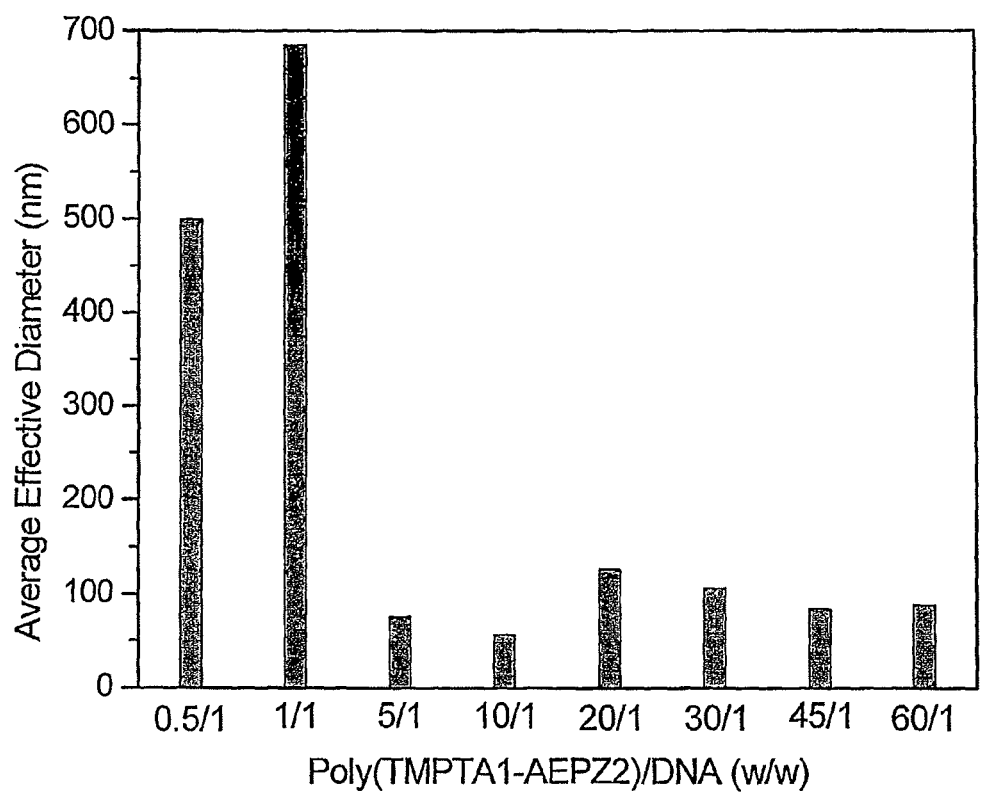
FIG. 6 illustrates a graphical representation of the average effective diameters of poly(TMPTA1-AEPZ2)/DNA (pCMV-Luc) complexes with different w/w ratios.
Figure 7:
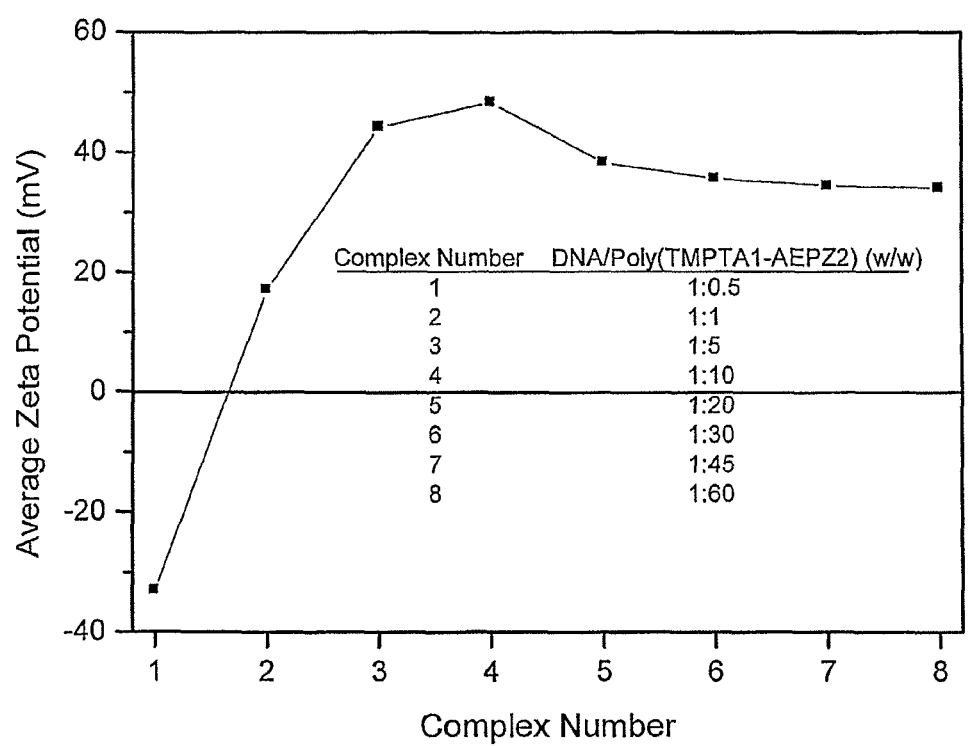
FIG. 7 illustrates a graphical representation of the average ξ-potentials of poly(poly(TMPTA1-AEPZ2)/DNA (pCMV-Luc)) complexes with different w/w ratios.

Effect of Weight Ratios on the Dimension and Shape of poly(amino ester)/DNA Complexes FIG. 6 shows poly(TMPTA1-AEPZ2) and DNA can form complexes having diameters raging from 50 to 150 nm at DNA/polymer ratios above 1:5. The results suggest the complexes formed at ratios above 1/5 can effectively enter a cell through endocytosis. The particle size data are also consistent with those of the -potentials shown in FIG. 7. In general, complexes can reach a maximum diameter as charge neutrality is achieved and aggregation occurs. FIG. 7 shows that charge neutrality occurs at a polymer/DNA ratio between 0.5 and 1 and the ξ-potentials as the particles approach a limiting value ranging from +30 to +50 mV at polymer/DNA ratios above 5/1, which have led to the formation of particles of small size by the prevention of aggregation. A similar trend is observed for poly(PETA1-AEPZ3)/DNA complexes.

Example 14

Cytotoxicity Assay of poly(amino ester)s 293 cells were cultured in DMEM supplemented with 10% FCS at 37° C., 10% $CO_2$, and 95% relative humidity. For the cell viability assay, polymer solutions were prepared in serum supplemented tissue culture medium. Osmolarity of the preparations and pH were routinely measured, for example, pH and osmolarity were adjusted to 7.4 and 280-320 mosm/kg, respectively. The cells (10,000 cells/well) were seeded into 96-well microliter plates (Nunc, Wiesbaden, Germany). After overnight incubation, the culture medium was replaced with 100 µl serial dilutions of the polymers, and the cells were incubated for another 12 h. Then, medium with polymer extraction was aspirated and replaced by 100 µl DMEM without serum to minimize the change of aggregate formation between the charged sites of proteins and polymer before adding 3-(4,5-dimethylthiazol-2-yl)-2,5-diphenyl tetrazolium bromide (MTT) assays. Sterile filtered MTT (20 µl, 5 mg/ml) stock solution in phosphate buffered saline (PBS) was added to each well to reach a final MTT concentration of 0.5 mg/ml. After 4 h, unreacted dye was removed by aspiration. The formazan crystals were dissolved in 100 µl/well DMSO (BDH laboratory Supplies, England) and measured spectrophotometrically in an ELISA reader (Model 550, Bio-Rad) at a wavelength of 570 nm. The spectrophotometer was calibrated to 0 absorbance using culture medium without cells. The relative cell growth (%) related to control cells containing cell culture medium without polymer was calculated by [A]test/[A]control×100. Similar low cytotoxicity is also observed for poly(PETA1-AEPZ3).

Example 15

Comparision of Cytotoxicity of poly(amino ester)s and PEIs

Figure 8:
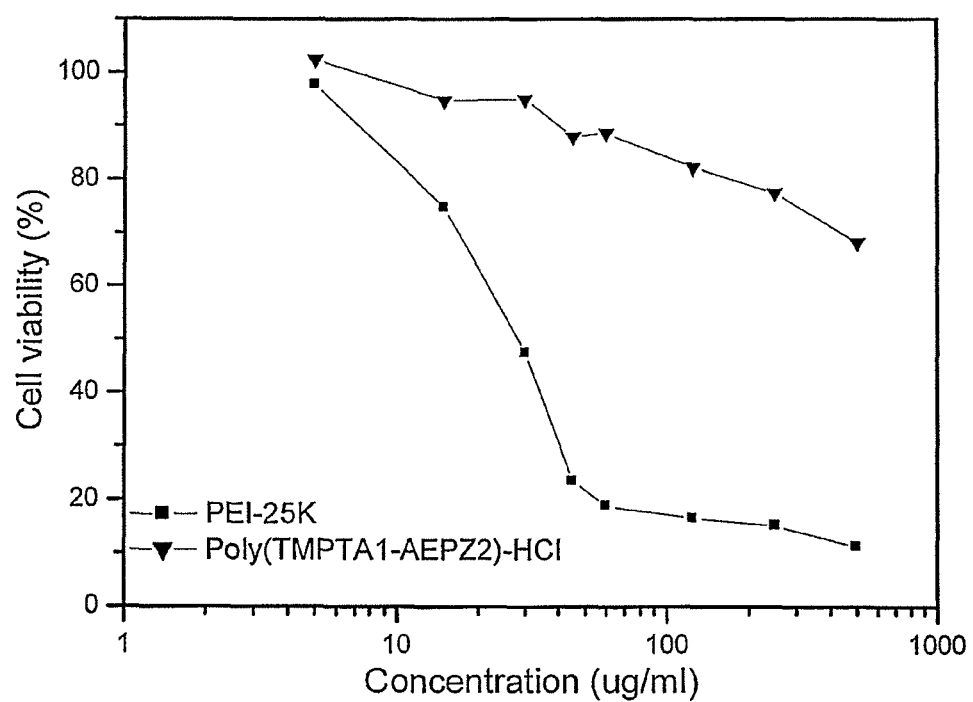
FIG. 8 illustrates a graphical comparison of the cytotoxicity profiles of a hyperbranched poly(TMPTA1-AEPZ2) with a PEI ($M_w$=25 kDa) in HEK 293 cells.

FIG. 8 shows the results of the cytotoxicity assay. Poly(TMPTA1-AEPZ2) has no effect on the cell viability up to a polymer concentration of 150 µg/ml. In comparison, poly(ethylenimine) (PEI) (25 K), one of the most efficient polymers for the delivery of DNA, shows apparent toxicity as reflected by the significant decreased cell viability at a polymer concentration of 40 µg/ml. Cytotoxicity assay is also conducted using poly(PETA1-AEPZ3) compounds. The experimental data show that the poly(PETA1-AEPZ3) compounds have no effect on cell viability up to a polymer concentration of 200 µg/ml.

Example 16

Cell Transfection Efficiency of Hyperbranched poly(amino ester)s

The in vitro transfection efficiency of poly(amino ester)s was evaluated in 293 cells using the complexes formed with poly(TMPTA1-AEPZ2) and pCAG-Luc DNA and poly(PETA1-AEPZ3)/pCAG-Luc DNA. Cells were seeded 24 h prior to transfection into 24-well plates (Becton-Dickinson, Lincoln Park, N.J.) at a density of $5 \times 10^4$ per well with 0.5 ml of complete medium. At the time of transfection, the medium in each well was replaced with 500 µl of serum free DMEM. Polymer/DNA complexes (100 µl) with various w/w (or N/P) at a DNA dose of 2 µg/well were dropped into each well and incubated with the cells for 4 h at 37° C. The medium was replaced with 0.5 ml of fresh complete medium and cells were further incubated for 48 h. After the incubation, the medium was drawn out and the well was washed with 0.3 ml 1×PBS, and cells were permeabilized with 200 µl of cell lysis buffer (1×) (Promega Co., Wis.). The complexes were cooled at −78° C. for 20 min, then returned to room temperature, cooled at −78° C. for 20 min again, returned to room temperature and collected into 0.6 ml of tubes. After centrifugation (15000/5 min at 4° C.), the samples were ready for testing. The luciferase activity in cell extracts was measured using a luciferase assay Kit (Promega Co., Madison, Wis.) on a single-well luminometer (Berthold Lumat LB 9507, Germany) for 10 s. The light units (LU) were normalized against protein concentration in the cell extracts, which was measured using a protein assay kit (Bio-Rad Labs, Hercules, Calif.). High transfection efficiency is also observed for poly(PETA1-AEPZ3)/DNA complexes.

Example 17

Effect of Weight Ratios on Transfection Efficiency of poly(amino ester)s

Figure 9:
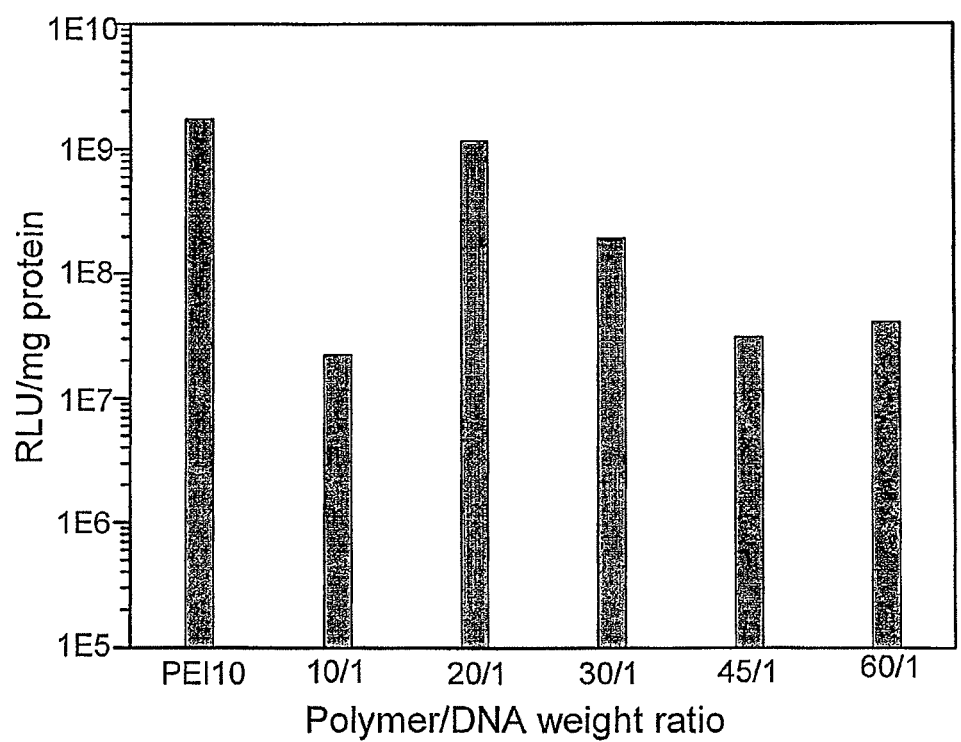
FIG. 9 illustrates a graphical comparison of the transfection efficiency of the hyperbranched poly(TMPTA1-AEPZ2)/DNA complexes in 293 cells with a PEI ($M_w$=25 kDa) mediated transfection under optimal conditions.

FIG. 9 displays the results for the complexes comprised of different weight ratios of polymer and DNA. Poly(TMPTA1-AEPZ2) yielded the highest transfection efficiency at a polymer/DNA weight ratio of 20:1, which was about 70% of control experiments employing poly(ethylenimine) (PEI) (25 k). It should be noted that the non-optimized transfection efficiency measured for poly(TMPTA1-AEPZ2) was obtained in the absence of chloroquine, a commonly used weak base to enhance in vitro transfection through facilitating the release of DNA vectors from endosomes. The high transfection efficiency of poly(TMPTA1-AEPZ2) is probably due to the existing primary amines which participate in forming complexes with DNA through ionic interaction with phosphate groups, and the buffer capability from the simultaneously existing secondary amines and tertiary amines, which facilitate the release of DNA from endosomes. High transfection efficiency is also observed for poly(PETA1-AEPZ3).

Example 18

Fluorescence Emission of Hyperbranched poly(amino ester)s

Hyperbranched poly(TMPTA1-AEPZ2)-HCl (30 mg) was dissolved in deionized water (4 ml) at a concentration of 7.5 mg/ml (w/V). The solution was shaken at room temperature for two hours, followed by adjust pH to 7 using NaOH solution (1.0 M). The colorless solution displays blue luminescence when irradiated by UV light at 365 nm. Poly(PETA1-AEPZ3) also has a UV-vis absorption and exhibit an even stronger fluorescence emission when excited by UV light. The fluorescence properties of poly(amino ester) having various molecular weights and degrees of branchings are also investigated.

Figure 10:
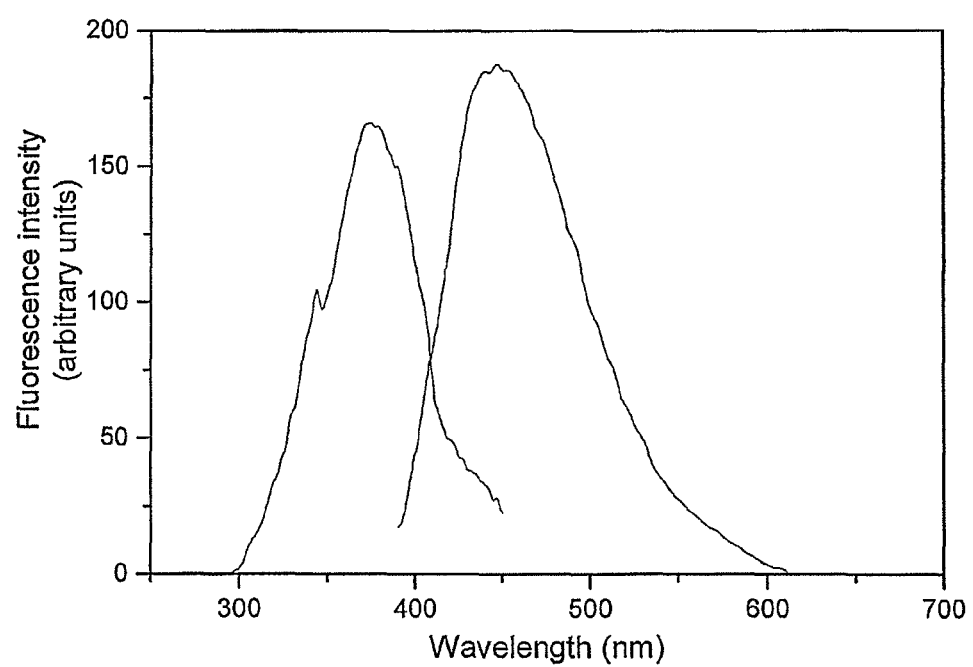
FIG. 10 illustrates both emission and excitation spectra of a hyperbranched poly(TMPTA1-AEPZ2) sample at pH=7. The sample is irradiated at 366 nm.

FIG. 10 shows both the excitation and emission fluorescence spectra of a hyperbranched poly(amino ester), such as poly(TMPTA1-AEPZ2). The poly(amino ester)s presents an excitation band at 366 nm and an emission band at 460 nm.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A branched poly(amino ester) compound having the formula:

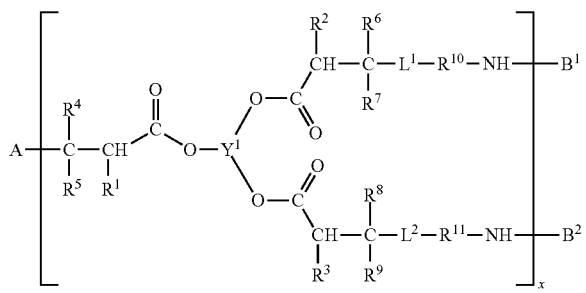

wherein x is an integer between 1 and about 10,000;

each of $R^1$, $R^2$ and $R^3$ is independently selected from the group consisting of hydrogen and hydrocarbyl;

each of $R^4$, $R^5$, $R^6$, $R^7$, $R^8$ and $R^9$ is independently selected from the group consisting of hydrogen and hydrocarbyl and alkyl;

each of $L^1$ and $L^2$ is $N(-R^{13}-)(-R^{14}-)Z$, wherein each of $R^{13}$ and $R^{14}$ is bonded to N and Z to form a cyclic structure, and wherein each of $R^{10}$, $R^{11}$, $R^{13}$ and $R^{14}$ is independently an optionally substituted $C_{1-30}$ alkylene; and each Z is independently selected from the group consisting of N, and CH, with the proviso that $R^1$, $R^2$, $R^3$, $R^4$, $R^5$, $R^6$, $R^7$, $R^8$, $R^9$ and $R^{12}$ cannot have a primary amino group, a secondary amino group, or a carbon-carbon double bond conjugated to a carbonyl group;

$Y^1$ is selected from the group consisting of (alkylene)$_3$CR$^c$, wherein each $R^c$ is independently selected from the group consisting of alkyl and aryl;

A is selected from the group consisting of optionally substituted piperazinyl, optionally substituted piperidinyl, optionally substituted azetidinyl, optionally substituted pyrrolidinyl, N-methyl piperazinyl, N-ethyl piperazinyl, and 1-methyl-4-methylamino-piperidinyl, and benzyl-1-piperazinyl carboxylate; and each of $B^1$ and $B^2$ is independently selected from the group consisting of H and hydrocarbyl.

2. The compound of claim 1, wherein A is selected from the group consisting of, optionally substituted piperazinyl, optionally substituted piperidinyl, optionally substituted azetidinyl and optionally substituted pyrrolidinyl.

3. The compound of claim 1, wherein x is an integer from 1 to about 2000.

4. The compound of claim 1, having a polydispersity between about 1 and about 4.

5. The compound of claim 1, wherein $Y^1$ is selected from the group consisting of $(CH_2)_3CR^c$ and $(CH_2)_3SiR^c$.

6. The compound of claim 1, wherein each of $R^4$, $R^5$, $R^6$, $R^7$, $R^8$ and $R^9$ is H; and $Y^1$ is $(CH_2)_3CR^c$.

7. The compound of claim 1, wherein $Y^1$ is $(CH_2)_3CCH_2CH_3$.

8. The compound of claim 1, wherein each of $R^4$, $R^5$, $R^6$, $R^7$, $R^8$ and $R^9$ is H; $R^1$, $R^2$ and $R^3$ are H or $C_1$-$C_8$ hydrocarbyl; each $R^{10}$ and $R^{11}$ is independently an optionally substituted $C_{1-30}$ alkylene; and $Y^1$ is selected from the group consisting of (alkylene)$_3$CCH$_2$CH$_3$ and (alkylene)$_3$SiCH$_2$CH$_3$.

9. A pharmaceutical composition comprising a bioactive agent and a compound according to claim 1.

* * * * *